United States Patent
Singhal et al.

(10) Patent No.: US 10,478,151 B2
(45) Date of Patent: Nov. 19, 2019

(54) SYSTEM AND METHOD FOR AUTOMATED MONITORING OF FETAL HEAD DESCENT DURING LABOR

(71) Applicant: General Electric Company, Schenectady, NY (US)

(72) Inventors: Nitin Singhal, Bangalore (IN); Kajoli Banerjee Krishnan, Bangalore (IN); Christian Fritz Perrey, Mondsee (AT); Klaus Pintoffl, Mondsee (AT); Walter Duda, Jr., Mondsee (AT); Francesca Patruno, Velizy (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1049 days.

(21) Appl. No.: 14/457,169

(22) Filed: Aug. 12, 2014

(65) Prior Publication Data
US 2016/0045152 A1 Feb. 18, 2016

(51) Int. Cl.
*A61B 8/08* (2006.01)
*A61B 5/00* (2006.01)
(Continued)

(52) U.S. Cl.
CPC .......... *A61B 8/0866* (2013.01); *A61B 5/1075* (2013.01); *A61B 5/1122* (2013.01);
(Continued)

(58) Field of Classification Search
CPC ... A61B 8/0866; A61B 8/5223; A61B 5/4362; A61B 5/1075; A61B 5/1128;
(Continued)

(56) References Cited

U.S. PATENT DOCUMENTS 5,222,485 A * 6/1993 Jerath .................. A61B 8/0866
600/437
5,876,357 A * 3/1999 Tomer .................. A61B 5/1076
600/587
(Continued)

FOREIGN PATENT DOCUMENTS

WO 2002098271 A2 12/2002
WO 2005077261 A1 8/2005
(Continued)

OTHER PUBLICATIONS

Barbera, Antonino F. "The Angle of Progression: An Objective Assessment of Fetal Head Descent in the Birth Canal." Intrapartum Ultrasonography for Labor Management (2012), pp. 87-100.*
(Continued)

*Primary Examiner* — Angela M Hoffa
(74) *Attorney, Agent, or Firm* — McAndrews, Held & Malloy, Ltd.; Jacob Groethe; David Bates

(57) ABSTRACT

A method for automatically monitoring fetal head descent in a birth canal is presented. The method includes segmenting each image in one or more images into a plurality of neighborhood components, determining a cost function corresponding to each neighborhood component in the plurality of neighborhood components in each of the one or more images, identifying at least two structures of interest in each image in the one or more images based on the cost function, wherein the at least two structures of interest include a pubic ramus and a fetal head, measuring an angle of progression based on the at least two structures of interest, and determining the fetal head descent in the birth canal based on the angle of progression.

17 Claims, 12 Drawing Sheets

(51) Int. Cl.
*A61B 5/107* (2006.01)
*A61B 5/11* (2006.01)
*A61B 5/055* (2006.01)

(52) U.S. Cl.
CPC .......... *A61B 5/1128* (2013.01); *A61B 5/4362* (2013.01); *A61B 8/5223* (2013.01); *A61B 5/055* (2013.01); *A61B 5/1079* (2013.01); *A61B 2503/02* (2013.01); *A61B 2576/00* (2013.01)

(58) Field of Classification Search
CPC . A61B 5/1122; A61B 5/1079; A61B 2576/00; A61B 5/055; A61B 2503/02
See application file for complete search history.

(56) References Cited

U.S. PATENT DOCUMENTS

| | | | | |
|---|---|---|---|---|
| 6,200,279 | B1* | 3/2001 | Paltieli | A61B 5/1076 600/426 |
| 6,464,639 | B1 | 10/2002 | Kim et al. | |
| 6,591,004 | B1 | 7/2003 | VanEssen et al. | |
| 6,669,653 | B2* | 12/2003 | Paltieli | A61B 17/42 600/588 |
| 7,207,941 | B2* | 4/2007 | Sharf | A61B 5/0031 600/438 |
| 7,850,625 | B2* | 12/2010 | Paltieli | A61B 5/061 128/916 |
| 8,292,831 | B2 | 10/2012 | Fausett et al. | |
| 8,840,557 | B2* | 9/2014 | Casciaro | A61B 8/0866 600/407 |
| 8,891,881 | B2* | 11/2014 | Gupta | A61B 8/0866 382/128 |
| 2003/0114779 | A1* | 6/2003 | Paltieli | A61B 17/42 600/588 |
| 2004/0236193 | A1* | 11/2004 | Sharf | A61B 5/0031 600/302 |
| 2006/0015036 | A1* | 1/2006 | Paltieli | A61B 17/42 600/558 |
| 2008/0167553 | A1* | 7/2008 | Paltieli | A61B 5/061 600/437 |
| 2008/0167581 | A1* | 7/2008 | Paltieli | A61B 5/1076 600/588 |
| 2008/0249755 | A1 | 10/2008 | Tek et al. | |
| 2009/0093716 | A1 | 4/2009 | Deischinger et al. | |
| 2011/0112403 | A1* | 5/2011 | MacHtey | A61B 8/02 600/443 |
| 2011/0257529 | A1* | 10/2011 | Casciaro | A61B 8/0866 600/443 |
| 2012/0249764 | A1 | 10/2012 | Kuon et al. | |
| 2013/0060119 | A1 | 3/2013 | Weeks et al. | |
| 2013/0190600 | A1* | 7/2013 | Gupta | A61B 8/0866 600/410 |
| 2013/0218015 | A1 | 8/2013 | Machtey et al. | |
| 2016/0074006 | A1* | 3/2016 | Patruno | A61B 8/0866 600/443 |
| 2017/0206659 | A1* | 7/2017 | Perrey | G06T 7/0046 |

FOREIGN PATENT DOCUMENTS

| | | |
|---|---|---|
| WO | 2005096707 A2 | 10/2005 |
| WO | 2010057665 A1 | 5/2010 |
| WO | 2013103818 A1 | 7/2013 |

OTHER PUBLICATIONS

Khalil et al. "Assessment of the progress of labor by the use of intrapartum ultrasound." Alexandria J of Medicine 48 (2012), pp. 295-301.*

Molina et al. "What is the most reliable ultrasound parameter for assessment of fetal head descent?" Ultrasound Obstet Gynecol 36 (2010), pp. 493-499.*

Fouche et al. "Ultrasound in monitoring of the second stage of labour." Gynecologie Obstetrique & Fertilite 40 (2012), pp. 658-665.*

Duckelmann et al., "Measurement of fetal head descent using the 'angle of progression' on transperineal ultrasound imaging is reliable regardless of fetal head station or ultrasound expertise.", Ultrasound Obstet Gynecol 2010, NCBI, vol. 35, pp. 216-222.

Bamberg C et al., "Angle of progression measurements of fetal head at term: a systematic comparison between open magnetic resonance imaging and transperineal ultrasound.", Department of Obstetrics, Charite University Hospital, Berlin, Germany., vol. 206, Issue 2 , Feb. 2012, pp. 261-262.

Casciaro et al., "Automatic Evaluation of Progression Angle and Fetal Head Station through Intrapartum Echographic Monitoring", Computational and Mathematical Methods in Medicine, Hindawi Publishing Corporation, 2013, 9 Pages.

Office Action for Chinese Patent Application No. 201580048924.1, dated May 10, 2019, 6 pages.

Kalache et al., "Transperineal ultrasound imaging in prolonged second stage of labor with occipitoanterior presenting fetuses: how well does the 'angle of progression' predict the mode of delivery?," Ultrasound Obstet Gynecol 2009, vol. 33, pp. 326-330.

International Search Report and Written Opinion from corresponding PCT application No. PCT/US2015/047673 dated Nov. 26, 2015; 15 pages.

A.F. Barbera et al., "A new method to assess fetal head descent in labor with transperineal ultrasound", Ultrasound in Obstetrics and Gynecology, vol. 33, No. 3, Mar. 1, 2009, pp. 313-319.

Foroughi P et al., "Ultrasound Bone Segmentation Using Dynamic Programming", Ultrasonics Symposium, 2007, IEEE, IEEE, Piscataway, NJ, USA, Oct. 1, 2007, pp. 2523-2526.

A.M. Duckelmann et al., "Measurement of fetal head descent using the 'angle of progression' on transperineal ultrasound imaging is reliable regardless of fetal head station or ultrasound expertise". Ultrasound in Obstetrics and Gynecology, vol. 35, No. 2, Feb. 1, 2010, pp. 216-222.

* cited by examiner

SYSTEM AND METHOD FOR AUTOMATED MONITORING OF FETAL HEAD DESCENT DURING LABOR

BACKGROUND

Embodiments of the present specification relate to imaging, and more particularly to automated measurement of fetal head descent in a birth canal during labor.

Ultrasound imaging has been employed for a wide variety of applications. During the process of ultrasound scanning, a clinician attempts to capture a view of a certain anatomy which confirms/negates a particular medical condition. Once the clinician is satisfied with the quality of a view or a scan plane, the image is frozen to proceed to a measurement phase. For example, ultrasound images are routinely used to assess gestational age (GA) and weight of a fetus or to monitor cardiac health of a patient. Subsequent to the selection of a desired image, ultrasound measurements of specific features of fetal anatomy such as the head, abdomen or the femur from two-dimensional (2D) or three-dimensional (3D) image data may be obtained. These measurements are used in the determination of GA, assessment of growth patterns, and identification of anomalies. Similarly, for cardiac applications, thicknesses of cardiac walls are routinely measured by cardiologists to check for cardiomyopathy.

In recent times, ultrasound scanning has also been used in labor and delivery applications. The current practice in labor and delivery is based on a digital examination to estimate the fetal head position. Digital examination of fetal descent using transvaginal imaging remains the "gold standard" for evaluating a fetal head station. Unfortunately, the digital examination is subjective and inaccurate with high inter-observer variability.

Recent studies have recommended use of transperineal ultrasound to allow for objective quantification of fetal head descent in the birth canal. In addition, use of multiple measurements in conjunction with transperineal ultrasound has been suggested for the quantification of the fetal head descent. There is growing evidence suggesting that an angle of progression may provide an objective, more reproducible and accurate tool to monitor progression of the fetal head in the birth canal during labor. However, manually measuring the angle of progression using the ultrasound images is a user-dependent and time-consuming method. Moreover, there is substantial variability in the measurement of angle of progression and interpretation of fetal station even among experienced clinicians. Consequently, this variability in the measurement of the angle of progression adversely affects clinical evaluation of the progress of labor. Additionally, two-dimensional transperineal ultrasound images having artifacts such as caput and/or molding further exacerbate the evaluation of the fetal head descent.

It is therefore desirable to enhance accuracy of measurement of the angle of progression that is independent of the experience of the user. In particular, it is desirable to automate the measurement of the angle of progression to enhance the skill and utilization of clinicians or paramedics across the world and also encourage adoption of ultrasound to assist labor in geographies with fewer experienced sonographers. The automated measurement of the angle of progression aids in reducing the variability in assisting patients during labor. Moreover, the automated measurement of the angle of progression will provide a consistent and objective measure that is independent of the experience of staff and/or doctors in the labor room.

Currently available techniques entail combining position tracking technology with advanced ultrasound imaging to objectively determine the fetal head station in the labor room. However, these techniques disadvantageously call for manual marking of points on the pelvis or entail use of a position sensor followed by marking known fetal head landmarks on the ultrasound image to determine the spatial position of the fetal head in relation to the pelvic bone. However, the need for manual intervention while using these techniques impedes the automation of the process of monitoring the fetal head descent during labor.

BRIEF DESCRIPTION

In accordance with aspects of the present specification, a method for automatically monitoring fetal head descent in a birth canal is presented. The method includes segmenting each image in one or more images into a plurality of neighborhood components. Moreover, the method includes determining a cost function corresponding to each neighborhood component in the plurality of neighborhood components in each of the one or more images. In addition, the method includes identifying at least two structures of interest in each of the one or more images based on the cost function, wherein the at least two structures of interest include a pubic ramus and a fetal head. Also, the method includes measuring an angle of progression based on the at least two structures of interest. Further, the method includes determining the fetal head descent in the birth canal based on the angle of progression. A non-transitory computer readable medium including one or more tangible media, where the one or more tangible media include code adapted to perform the method for automatically monitoring fetal head descent in a birth canal is also presented.

In accordance with another aspect of the present specification, a system is presented. The system includes a fetal head descent monitoring platform, configured to obtain one or more images corresponding to a birth canal of a patient in labor, segment each of the one or more images into a plurality of neighborhood components, determine a cost function corresponding to each neighborhood component in the plurality of neighborhood components in each of the one or more images, identify at least two structures of interest in each of the one or more images based on the cost function, wherein the at least two structures of interest include a pubic ramus and a fetal head, measure an angle of progression based on the at least two structures of interest, and determine fetal head descent in the birth canal based on the angle of progression.

In accordance with yet another aspect of the present specification, an imaging system is presented. The imaging system includes an acquisition subsystem configured to obtain one or more images corresponding to a region of interest in an object of interest. In addition, the imaging system includes a processing subsystem in operative association with the acquisition subsystem. Furthermore, the processing subsystem includes a fetal head descent monitoring platform, wherein the fetal head descent monitoring platform is configured to segment each of the one or more images into a plurality of neighborhood components, determine a cost function corresponding to each neighborhood component in the plurality of neighborhood components in each of the one or more images, identify at least two structures of interest in each of the one or more images based on the cost function, wherein the at least two structures of interest include a pubic ramus and a fetal head, measure an angle of progression based on the at least two structures of interest, and determine fetal head descent in the region of interest in the object of interest based on the angle of progression.

DRAWINGS

These and other features, aspects, and advantages of the present disclosure will become better understood when the following detailed description is read with reference to the accompanying drawings in which like characters represent like parts throughout the drawings, wherein.

Figure 1:
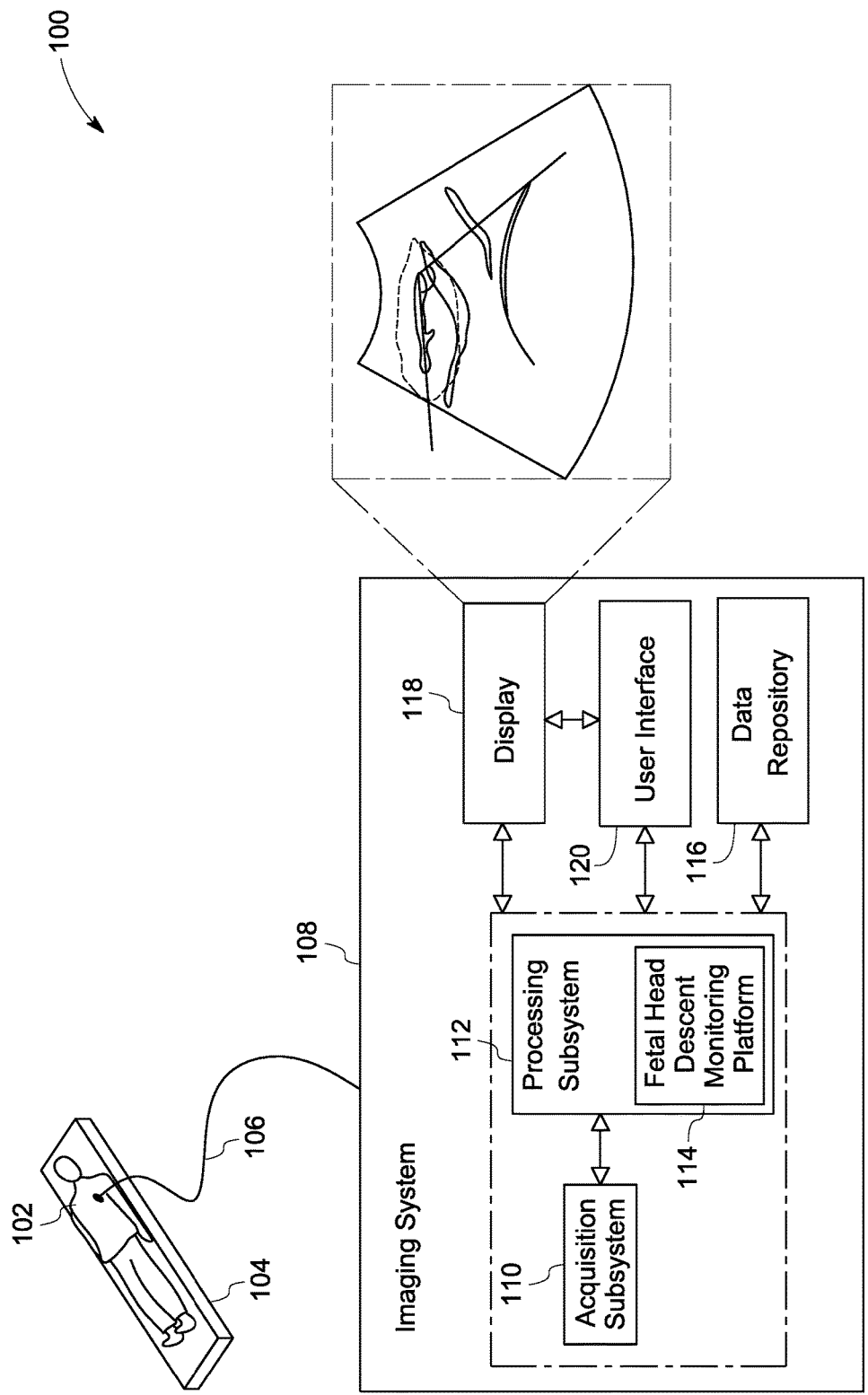
FIG. 1 is a diagrammatical illustration of a system for automated measurement of fetal head descent, in accordance with aspects of the present specification.
Figure 4:
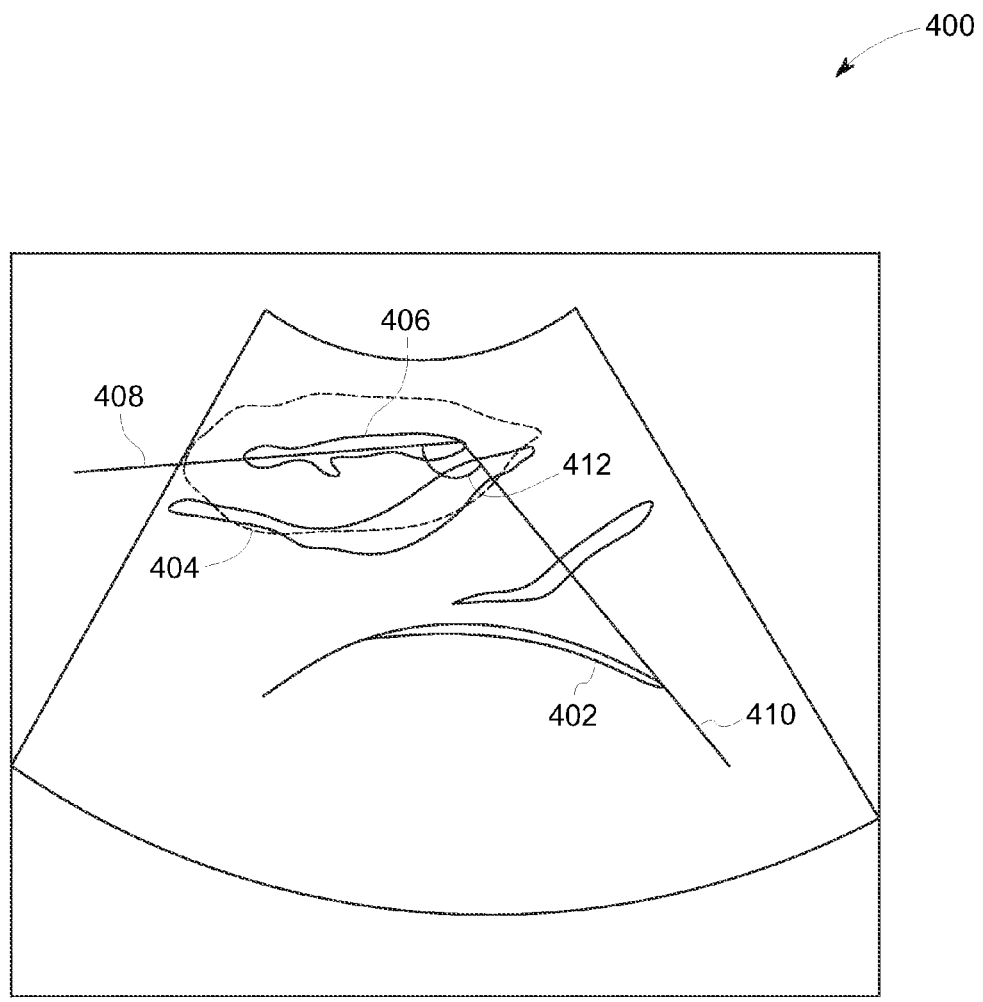
FIG. 4 is a diagrammatical illustration of an transperineal ultrasound image that show typical landmarks in the transperineal ultrasound image.
Figure 7:
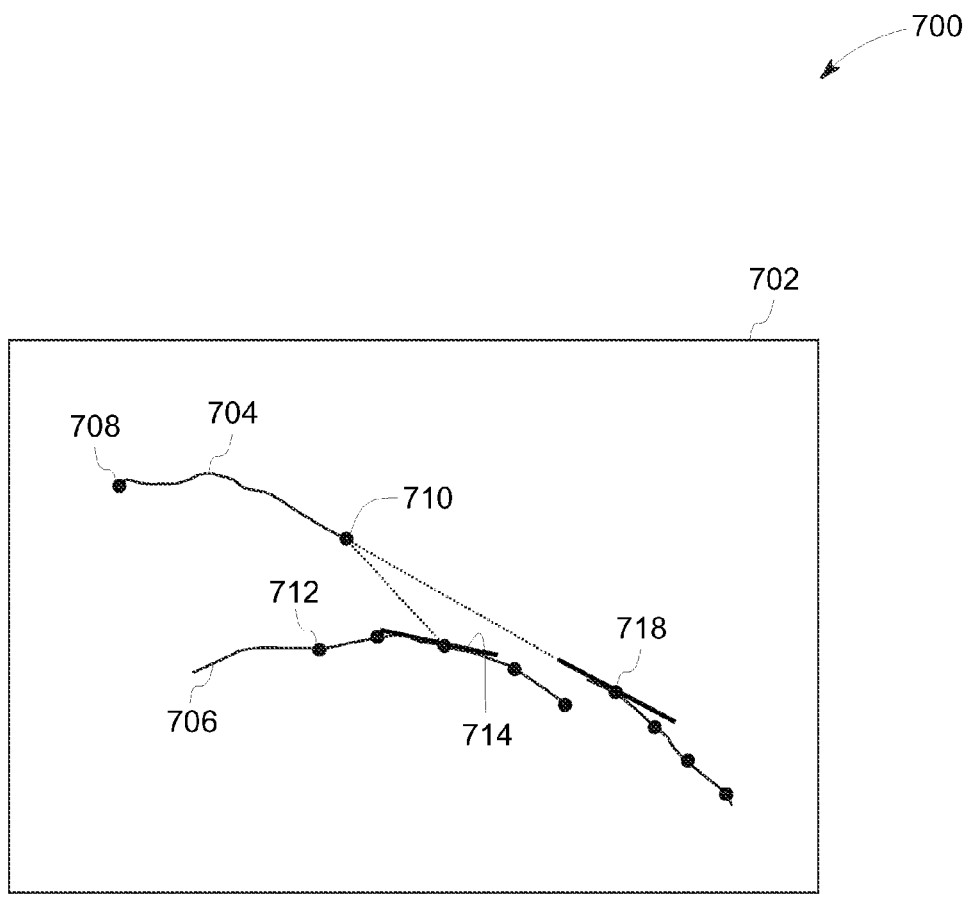
Figure 8:
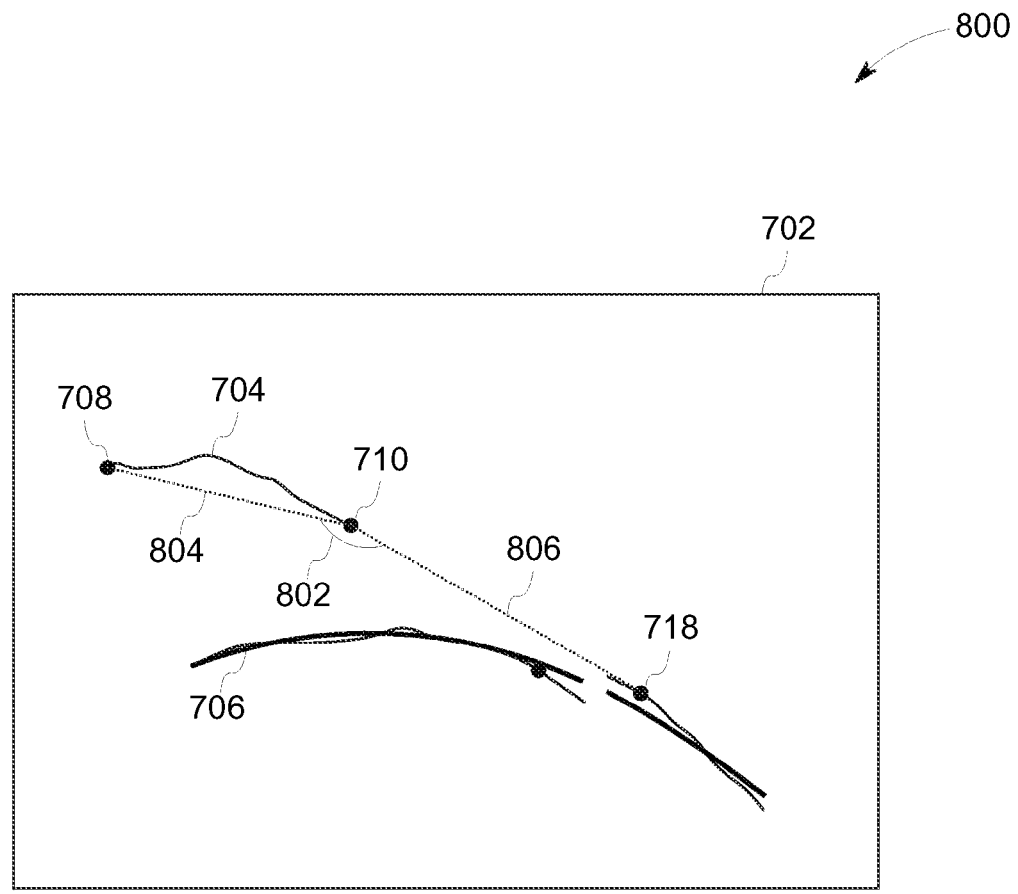
Figure 9:
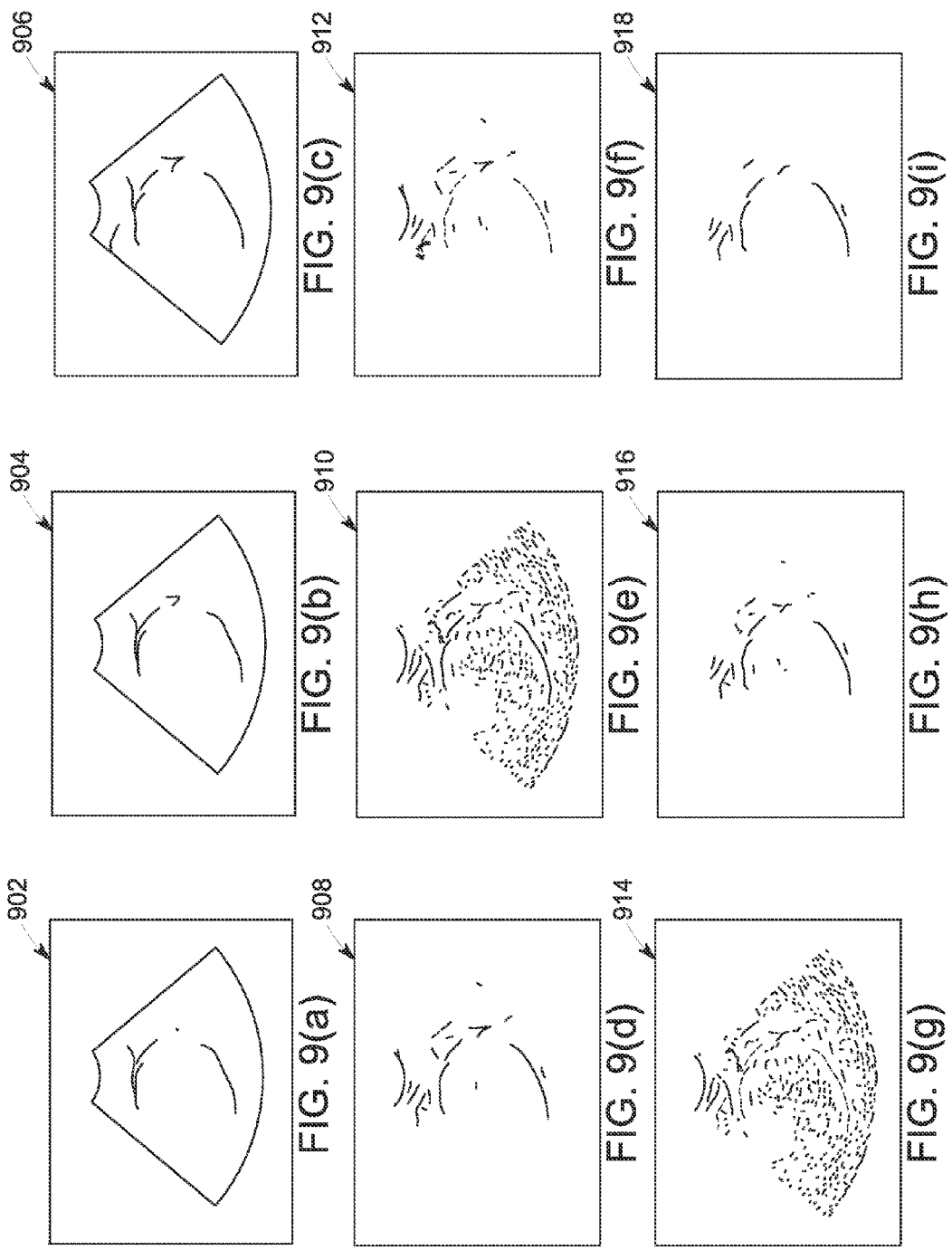
Figure 10:
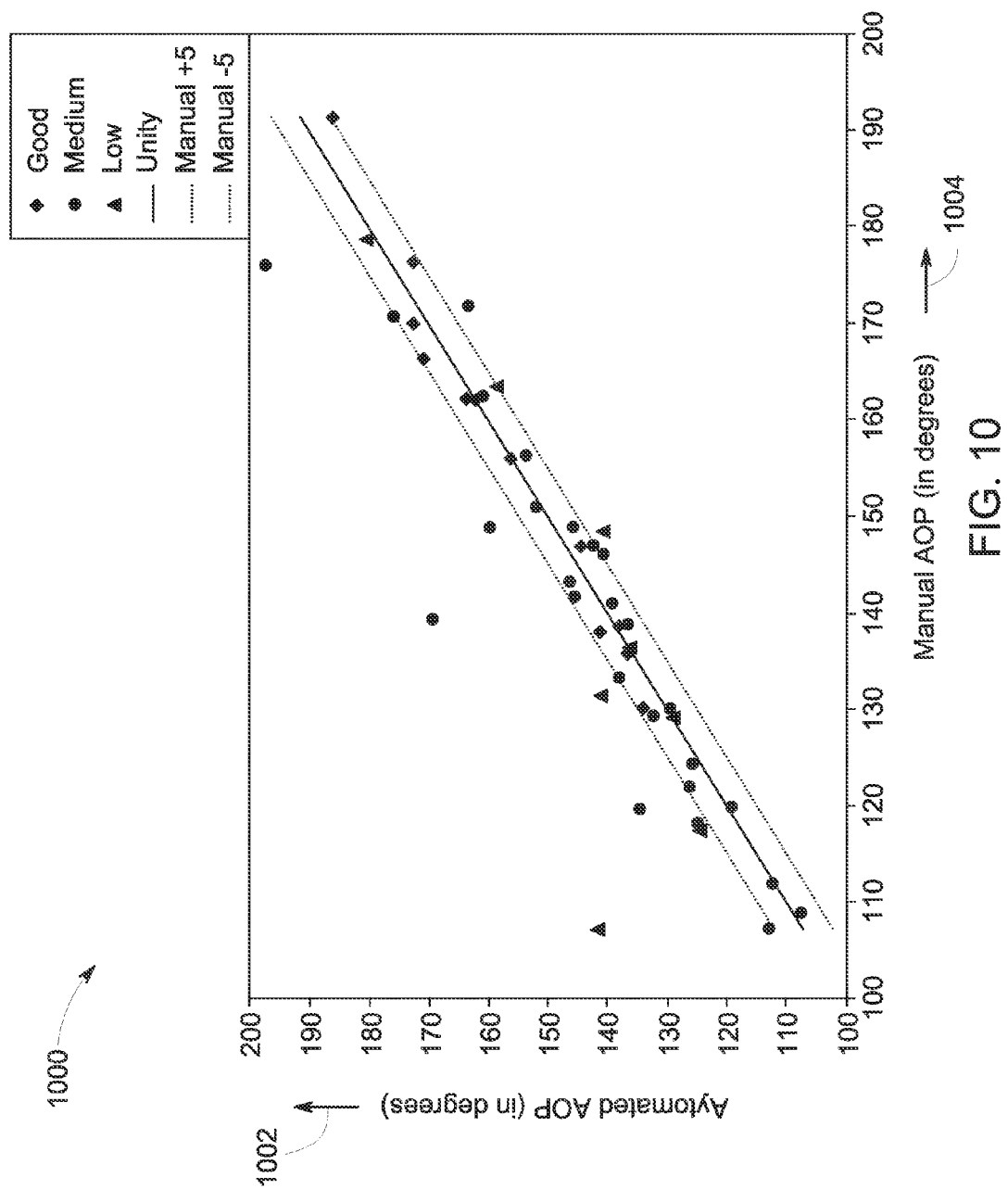
Figure 11:
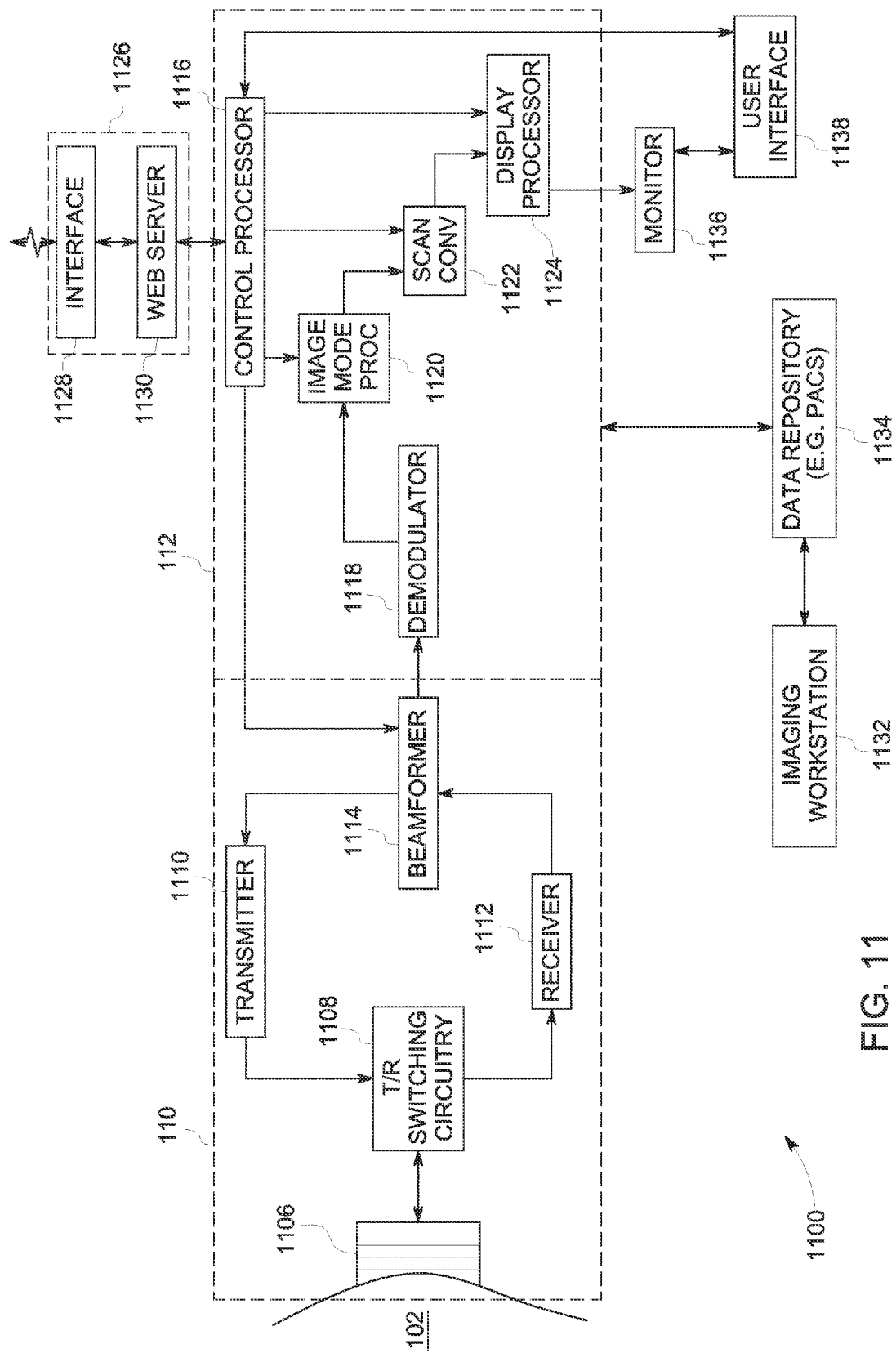

FIGS. 6(a)-6(f) are diagrammatical representations of a method of joining disjointed components for use in the selection of a desired anatomical structure of interest such as the pubic ramus, in accordance with aspects of the present specification;

FIG. 7 is a diagrammatical representation of computation of a tangent point for measuring descent of a fetal head, in accordance with aspects of the present specification;

FIG. 8 is a diagrammatical representation of measurement of an angle of progression for measuring descent of a fetal head, in accordance with aspects of the present specification;

FIGS. 9(a)-9(i) are diagrammatical representations of the method of FIG. 4, in accordance with aspects of the present specification;

FIG. 10 depicts a comparison of a traditional manual measurement of the angle of progression with the fully automated measurement of the AOP afforded by the system of FIG. 1; and FIG. 11 is a block diagram representation of one embodiment of an ultrasound imaging system for use in the system of FIG. 1.

DETAILED DESCRIPTION

As will be appreciated, during the process of childbirth, a clinician, such as a physician or a midwife monitors descent of a fetal head in a birth canal of a patient in labor. In accordance with exemplary aspects of the present specification, systems and methods configured to aid in enhancing clinical workflow are presented. In particular, the methods and systems are configured to facilitate automated monitoring of the fetal head descent during labor. Additionally, the systems and methods provide an objective and reproducible tool for monitoring the fetal head descent, while reducing variability in assisting patients during labor.

FIG. 1 is a block diagram of an exemplary system 100 for use in diagnostic imaging, in accordance with aspects of the present specification. More particularly, the system 100 is configured to aid the clinician in monitoring the fetal head descent in a birth canal of a patient 102 during labor.

During labor and delivery, the clinician, typically positions an ultrasound probe on or about a region of interest to be imaged. In the present example, the patient in labor 102 may be positioned in a supine position on a patient support 104. Furthermore, an image acquisition device 106 that is operatively coupled to a medical imaging system 108 may be used to acquire image data corresponding to an object of interest in the patient 102. In one embodiment, the image acquisition device 106 may be an ultrasound probe. Additionally, in one example, the medical imaging system 108 may be an ultrasound imaging system. The ultrasound imaging system 108 may be configured to receive ultrasound image data corresponding to the patient 102 and process the ultrasound image data to generate one or more images corresponding to the patient 102. It may be noted that the system 100 may be configured to automatically monitor fetal head descent in the birth canal during labor using a single acquired image. However, in certain other embodiments, more than one image may be employed to automatically monitor fetal head descent in the birth canal during labor.

Moreover, in one example, the one or more images may include transperineal ultrasound images. As will be appreciated, transperineal ultrasound images are representative of images that are acquired using an ultrasound imaging system that is optimized and configured to acquire the images when a probe is placed and roved over the peritoneum of the human anatomy to visualize anatomies of the pelvic region. In this example, the probe 106 may be placed transversely on a suprapubic region of the patient's abdomen. Furthermore, to determine progression of labor, the ultrasound probe 106 may be positioned on the perineum in a midsagittal position between the labia below the pubic symphysis. Moreover, a lateral position of the probe 106 may be adjusted until an image showing the sagittal view with one or more anatomical structures of interest or landmarks is obtained. In one example, the anatomical structures of interest may include a pubic ramus and a fetal head. It may be noted that the terms fetal head and fetal skull may be used interchangeably.

Furthermore, in one example, the acquired image may include a two-dimensional (2D) transperineal ultrasound image. Also, in certain embodiments, the images may include B-mode ultrasound images. Additionally, the 2D images may include static 2D images or cine loops that include a series of 2D images or image frames acquired over time. It may be noted that although the present specification is described in terms of 2D ultrasound images, use of the present specification with three-dimensional (3D) ultrasound images and four-dimensional (4D) ultrasound images is also envisaged. Also, the acquired image data may include cine loops, where the cine loops include 2D images acquired over time t.

In the present example, the object of interest may include a fetus in the patient 102. It may be noted that although the present specification is described with reference to a fetus as the object of interest, use of the present specification for imaging anatomical regions of interest in other objects of interest such as an adult patient is also envisaged. In a presently contemplated configuration, the system 100 may be configured to acquire image data representative of the fetus in the patient 102 during labor. In one embodiment, the system 100 may acquire image data corresponding to the fetus via an image acquisition device 106. Also, in one embodiment, the image acquisition device 106 may include a probe, where the probe may include an invasive probe, or a non-invasive or external probe, such as an external ultrasound probe, that is configured to aid in the acquisition of image data. Also, in certain other embodiments, image data may be acquired via one or more sensors (not shown) that may be disposed on the patient 102. By way of example, the sensors may include physiological sensors (not shown) such as positional sensors. In certain embodiments, the positional sensors may include electromagnetic field sensors or inertial sensors. These sensors may be operationally coupled to a data acquisition device, such as an imaging system, via leads (not shown), for example.

The system 100 may also include a medical imaging system 108 that is in operative association with the image acquisition device 106. It should be noted that although the exemplary embodiments illustrated hereinafter are described in the context of a medical imaging system, other imaging systems and applications such as industrial imaging systems and non-destructive evaluation and inspection systems, such as pipeline inspection systems, liquid reactor inspection systems, are also contemplated. Additionally, the exemplary embodiments illustrated and described hereinafter may find application in multi-modality imaging systems that employ ultrasound imaging in conjunction with other imaging modalities, position-tracking systems or other sensor systems. For example, the multi-modality imaging system may include a positron emission tomography (PET) imaging system-ultrasound imaging system. Furthermore, it should be noted that although the exemplary embodiments illustrated hereinafter are described in the context of a medical imaging system, such as an ultrasound imaging system, use of other imaging systems, such as, but not limited to, a computed tomography (CT) imaging system, a contrast enhanced ultrasound imaging system, an X-ray imaging system, an optical imaging system, a positron emission tomography (PET) imaging system, a magnetic resonance (MR) imaging system and other imaging systems is also contemplated in accordance with aspects of the present specification.

As noted hereinabove, in a presently contemplated configuration, the medical imaging system 108 may include an ultrasound imaging system. The medical imaging system 108 may include an acquisition subsystem 110 and a processing subsystem 112, in one embodiment. Further, the acquisition subsystem 110 of the medical imaging system 108 is configured to acquire image data representative of patient in labor 102 via the image acquisition device 106, in one embodiment. For example, the acquired image data may include a plurality of 2D transperineal ultrasound images or slices. It may be noted that the terms images and image frames may be used interchangeably. Additionally, the image data acquired from the fetus may then be processed by the processing subsystem 112.

According to aspects of the present specification, the image data acquired and/or processed by the medical imaging system 108 may be employed to aid a clinician in determining the progression of labor in the patient 102. In certain embodiments, the processing subsystem 112 may be further coupled to a storage system, such as the data repository 116, where the data repository 116 is configured to store the acquired image data. In certain embodiments, the data repository 116 may include a local database.

In addition, the acquisition subsystem 110 may also be configured to acquire images stored in the optical data storage article. It may be noted that the optical data storage article may be an optical storage medium, such as a compact disc (CD), a digital versatile disc (DVD), multi-layer structures, such as DVD-5 or DVD-9, multi-sided structures, such as DVD-10 or DVD-18, a high definition digital versatile disc (HD-DVD), a Blu-ray disc, a near field optical storage disc, a holographic storage medium, or another like volumetric optical storage medium, such as, for example, two-photon or multi-photon absorption storage format. Further, the 2D images so acquired by the acquisition subsystem 110 may be stored locally on the medical imaging system 108.

Furthermore, in accordance with exemplary aspects of the present specification, the processing subsystem 112 may include a fetal head descent monitoring (FHDM) platform 114 that is configured to aid in the automated determination of labor progression by automatically monitoring the fetal head descent in the birth canal of the patient in labor 102. The exemplary system 100 that includes the FHDM platform 114 provides a fully automated framework for determining a fetal head station in the patient in labor aids in simplifying the workflow and enhances the productivity of a skilled and/or less-experienced user. It may be noted that the term fetal head station is used to refer to a position of the head of the fetus in the birth canal of the patient in labor.

Also, in the presently contemplated configuration illustrated in FIG. 1, the processing subsystem 112 is shown as including the FHDM platform 114, where the FHDM platform 114 is configured to aid in the automated monitoring of the progression of labor using the acquired 2D ultrasound images. However, in certain embodiments, the FHDM platform 114 may also be used as a standalone module that is physically separate from the processing subsystem 112 and the medical imaging system 108. By way of example, the FHDM platform 114 may be external to and operatively coupled to the medical imaging system 108.

As noted hereinabove, traditionally, an angle of progression (AOP) is measured as an angle between the line joining the pubic symphysis and the line joining the fetal head. However, the pubic symphysis is a low echogenic structure, and hence difficult to segment especially with an automated technique. In accordance with exemplary aspects of the present specification, highly echogenic structures such as, but not limited to, the pubic ramus and the fetal head are used to determine the AOP in a speedy and accurate manner.

More particularly, the FHDM platform 114 may be configured to determine a position of the fetal head in the birth canal of the patient in labor 102 based on an angle of progression. As used herein, the term "angle of progression" is used to refer to an angle between two bony landmarks such as the fetal skull and the maternal pubic ramus using the 2D transperineal ultrasound images. In accordance with exemplary aspects of the present specification, the pubic ramus is used instead of the traditionally used pubic symphysis. The pubic ramus is a high echogenic structure in comparison to the low echogenic pubic symphysis. Use of the pubic ramus allows visualization of a clear structure of the landmark and also provides standardization of the measurement of the angle of progression.

The FHDM platform 114 may be configured to process the 2D images to automatically identify the pubic ramus and the fetal skull and to determine the angle of progression. In one example, the FHDM platform 114 may be configured to access the 2D images, from the local database 116. Alternatively, the 2D images may be obtained by the acquisition subsystem 110 from an archival site, a database, or an optical data storage article.

The 2D images may include at least two anatomical structures of interest such as the pubic ramus and the fetal head or fetal head contour. The pubic ramus is a curved structure with two end points. Also, a line passing through those two points may be referred to as a ramus line. Moreover, a line starting from the inferior apex of the pubic ramus (for example, the right end point) and intersecting the fetal skull contour tangentially may be referred to as a tangent line. In accordance with aspects of the present specification, the angle of progression is defined as the angle between the ramus line and the tangent line.

It may therefore be desirable to determine locations of anatomical structures of interest such as the pubic ramus and the fetal head/fetal skull contour in the 2D images. In one embodiment, the FHDM platform 114 may be configured to automatically measure the AOP using the 2D transperineal ultrasound images to provide an objective measure of the progression of labor.

Accordingly, the FHDM platform 114 may be configured to automatically detect two bony landmarks such as the pubic ramus and the fetal skull contour in the 2D images. In one embodiment, the FHDM platform 114 may be configured to segment the input image into neighborhood components using a series of morphological operations such as, but not limited to, vesselness, mean curvature, and neighborhood component labeling. As used herein, the term "neighborhood components" is used to refer to components that have substantially similar and/or homogeneous intensities.

Furthermore, the FHDM platform 114 may be configured to identify the pubic ramus and the fetal skull in the input images based on an objective function. In one example, the objective function may be based on anatomical presentation, location and size of the two bony landmarks (anatomical structures of interest) in the images. Once the pubic ramus and the fetal skull are identified, the FHDM platform 114 may also be configured to determine a ramus line and a tangent line. Accordingly, the FHDM platform 114 may be configured to determine a tangent point on the fetal skull. In one embodiment, the FHDM platform 114 may be configured to determine the tangent point on the fetal skull using an adaptive fetal skull contour modeling. In one example, the adaptive fetal skull contour model may be based on the nature of disjointedness of fetal skull. Additionally, the FHDM platform 114 may be configured to determine/measure the angle of progression. As previously noted, the angle of progression is defined as the angle between the ramus line and the tangent line. Furthermore, the objective function may also be adapted to determine a quality score corresponding to the 2D transperineal ultrasound images. The quality score may be utilized to assess the consistency of the images with clinical guidelines and appropriateness of use of these images to measure the angle of progression. The working of the FHDM platform 114 will be described in greater detail with reference to FIGS. 5-9.

Moreover, as illustrated in FIG. 1, the medical imaging system 108 may include a display 118 and a user interface 120. In certain embodiments, such as in a touch screen, the display 118 and the user interface 120 may overlap. Also, in some embodiments, the display 118 and the user interface 120 may include a common area. In accordance with aspects of the present specification, the display 118 of the medical imaging system 108 may be configured to display an image generated by the medical imaging system 108 based on the acquired image data. Additionally, in accordance with further aspects of the present specification, the progression of labor characterized by the fetal head descent determined by the FHDM platform 114 may be visualized on the display 118. Moreover, any quality metrics/indicators generated by the FHDM platform 114 may also be visualized on the display 118. In one embodiment, the indicator that is representative of the quality metric may be overlaid on the corresponding image visualized on the display 118. For example, the generated indicator may be overlaid on or about the image visualized on the display 118.

In addition, the user interface 120 of the medical imaging system 108 may include a human interface device (not shown) configured to aid the clinician in manipulating image data displayed on the display 118. The human interface device may include a mouse-type device, a trackball, a joystick, a stylus, or a touch screen configured to facilitate the clinician to identify the one or more regions of interest in the images. However, as will be appreciated, other human interface devices, such as, but not limited to, a touch screen, may also be employed. Furthermore, in accordance with aspects of the present specification, the user interface 120 may be configured to aid the clinician in navigating through the images acquired by the medical imaging system 106. Additionally, the user interface 120 may also be configured to aid in manipulating and/or organizing the displayed images and/or generated indicators displayed on the display 118.

Figure 2:
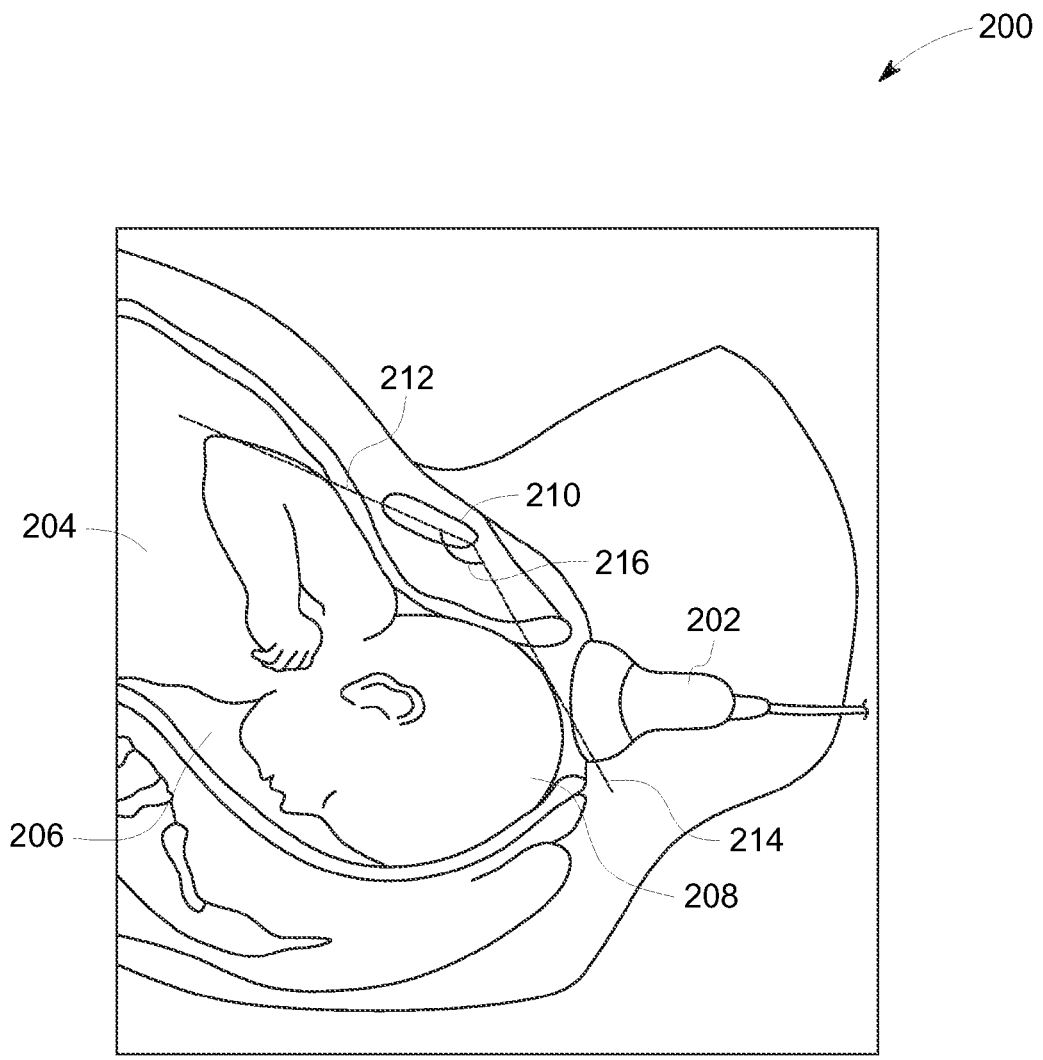
FIG. 2 is a diagrammatical illustration of one embodiment of use of the system of FIG. 1, in accordance with aspects of the present specification.

FIG. 2 is a diagrammatical representation 200 of one example of use of the system 100 of FIG. 1. In particular, use of transperineal ultrasound scanning for acquiring two-dimensional (2D) transperineal ultrasound images is depicted. In the transperineal ultrasound scanning method, an ultrasound probe 202 is generally positioned on the perineum in a mid-sagittal position between the labia below the pubic symphysis of a patient in labor, such as the patient 102 of FIG. 1. Furthermore, a lateral position of the probe 202 may be adjusted until an image showing the sagittal view that includes at least two anatomical structures of interest such as the pubic ramus and the fetal skull landmarks is obtained. Reference numeral 204 is representative of a fetus in a birth canal 206, while a contour of the fetal head is generally represented by reference numeral 208. Also, a capsule of pubic symphysis is represented by reference numeral 210.

Traditionally, an angle of progression (AOP) 216 is measured as an angle between a line 212 joining the pubic symphysis 210 and a line 214 joining the fetal head 208. However, the pubic symphysis 210 is a low echogenic structure. Consequently, segmenting the pubic symphysis using an automated technique is challenging. Hence, measuring the AOP using the currently available techniques entails manual intervention.

Figure 3:
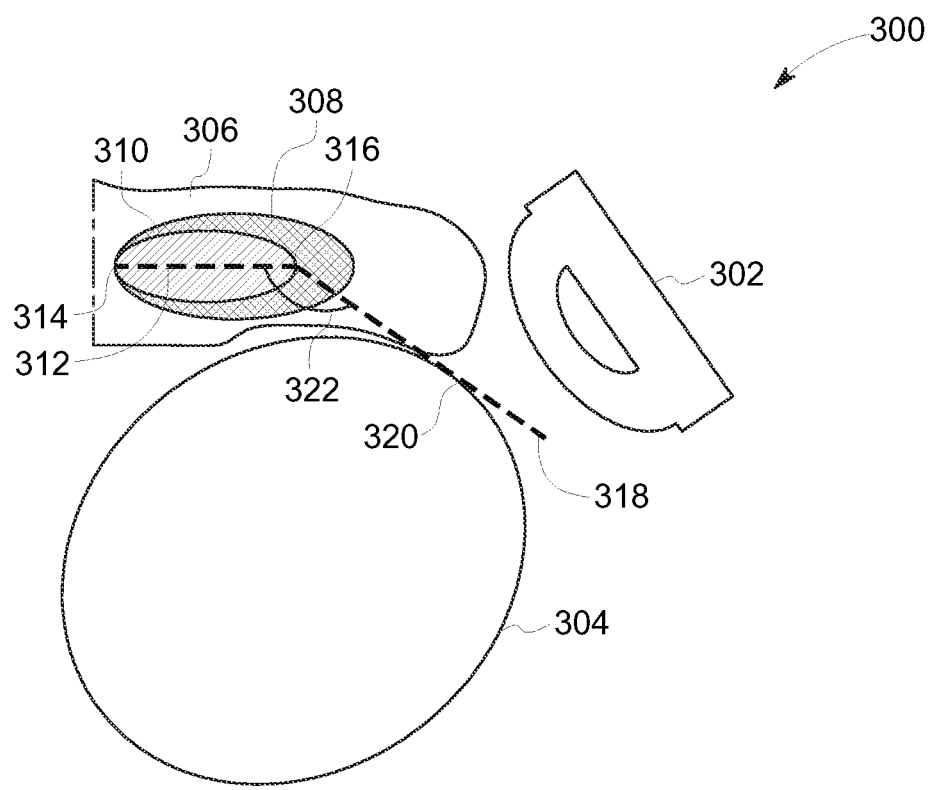
FIG. 3 is a diagrammatical illustration of a portion of FIG. 2 depicting measurement of an angle of progression using the system of FIG. 1, in accordance with aspects of the present specification.

The shortcomings of the currently available techniques may be circumvented via use of high echogenic structures in a transperineal ultrasound image. In accordance with aspects of the present specification, highly echogenic structures such as, but not limited to, a pubic ramus and a fetal head may be used to determine an AOP. FIG. 3 is a diagrammatical representation 300 of a method of measuring the AOP using the system 100 of FIG. 1, in accordance with aspects of the present specification. An image acquisition device, such as an ultrasound probe 302 may be employed to acquire image data corresponding to an anatomical region of a patient in labor. In one embodiment, the ultrasound probe 302 may be placed transversely on a suprapubic region of a patient's abdominal region to facilitate acquisition of image data from the patient.

Reference numeral 304 is representative of a fetal head or fetal head contour. Furthermore, reference numeral 306 may be generally representative of the symphysis capsule, while a pubic symphysis may be generally indicated by reference numeral 308. In accordance with aspects of the present specification, a pubic ramus 310 is employed to measure the AOP as opposed to use of the low echogenic pubic symphysis by the currently available techniques. The pubic ramus 310 is a curved structure with two end points 314, 316. Also, a first line passing through the two end points 314, 316 may be referred to as a ramus line 312. Additionally, a second line starting from the inferior apex of the pubic ramus (for example, the right end point 316) and intersecting the fetal skull contour 304 tangentially may be referred to as a tangent line 318. A point where the tangent line 318 intersects the fetal head 304 may be referred to as a tangent point 320. In accordance with aspects of the present specification, the AOP is defined as the angle 322 between the ramus line 312 and the tangent line 318.

Referring now to FIG. 4, a typical transperineal ultrasound image 400 is depicted. In one example, the ultrasound image 400 may be acquired by positioning the ultrasound image probe 302 (see FIG. 3) as depicted in FIG. 3. As previously noted, the position of the probe may be adjusted until at least two bony landmarks such as the pubic ramus and the fetal skull are clearly visualized in the image. The image 400 shows landmarks in a typical transperineal ultrasound image. A fetal head is indicated by reference numeral 402. Also, reference numeral 404 depicts a pubic symphysis capsule, while a pubic ramus is indicated by reference numeral 406.

As previously noted with reference to FIG. 2, the angle of progression, such as the AOP 216 of FIG. 2 is traditionally measured as an angle between the line joining the pubic symphysis and the line joining the fetal head. Disadvantageously, the pubic symphysis is a low echogenic structure, and hence difficult to segment especially with an automated technique. The shortcomings of the currently available techniques may be circumvented via use of high echogenic structures in the transperineal ultrasound image 400. In one embodiment, highly echogenic structures such as, but not limited to, the pubic ramus 406 and the fetal head 402 may be used to determine an angle of progression in a speedy and accurate manner. In addition to being highly echogenic structures, the pubic ramus 406 and the fetal head 402 are capable of being detected automatically.

In accordance with aspects of the present specification, an AOP 412 is measured as an angle subtended between a line 408 that joins the two end points of the pubic ramus 406 and a second line 410 that joins one end point of the pubic ramus 406 to the fetal head 402 tangentially. Accordingly, it is desirable to detect the pubic ramus and the fetal skull contour in the image. Moreover, in accordance with further aspects of the present specification, it is also desirable to identify a point where a line from the one end point of the pubic ramus 406 such as an inferior apex of the pubic ramus 406 intersects the fetal skull contour 402 tangentially.

Figure 5A:
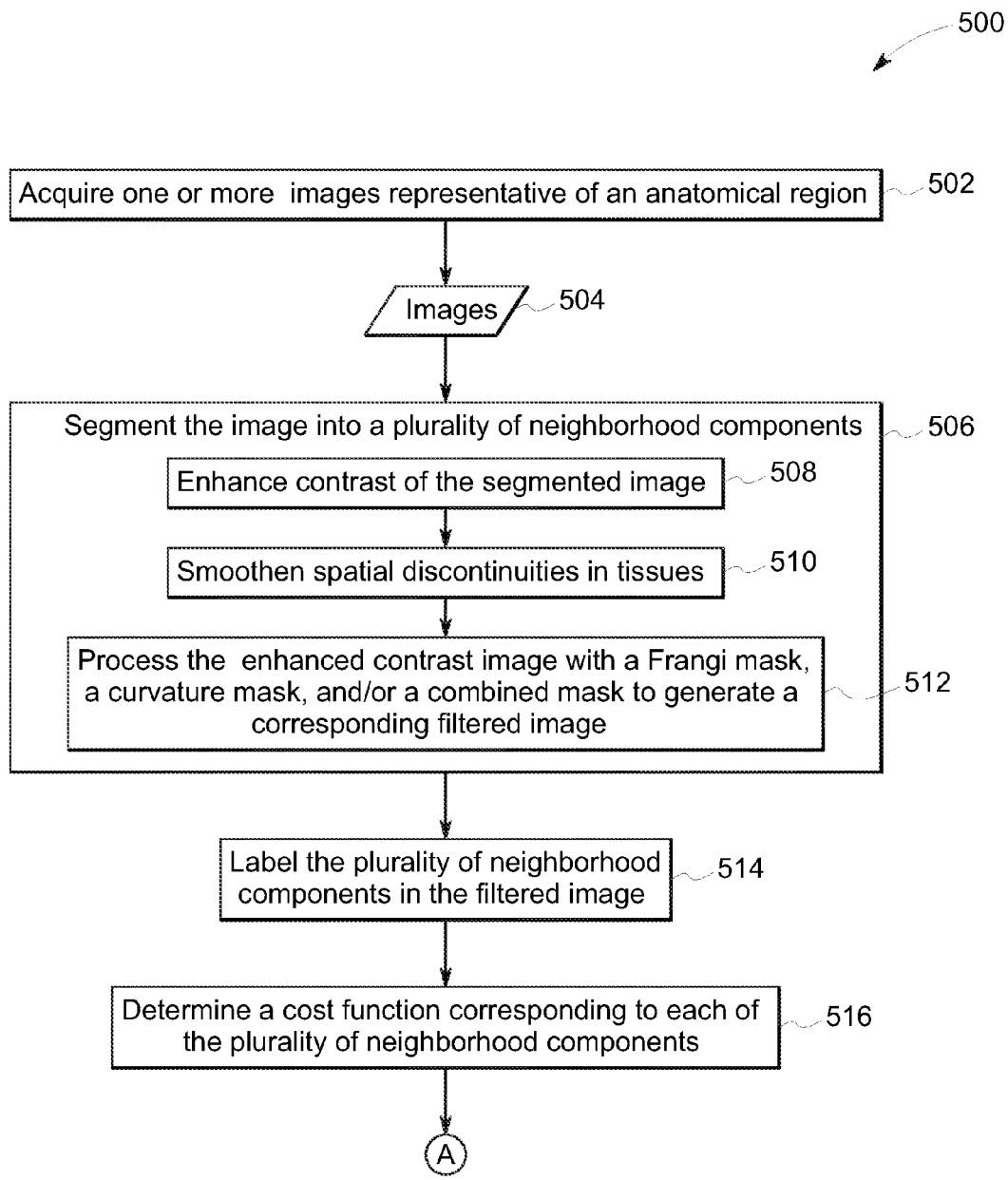
FIG. 5 is a flow chart depicting an exemplary method for automated measurement of fetal head descent, in accordance with aspects of the present specification.
Figure 5B:
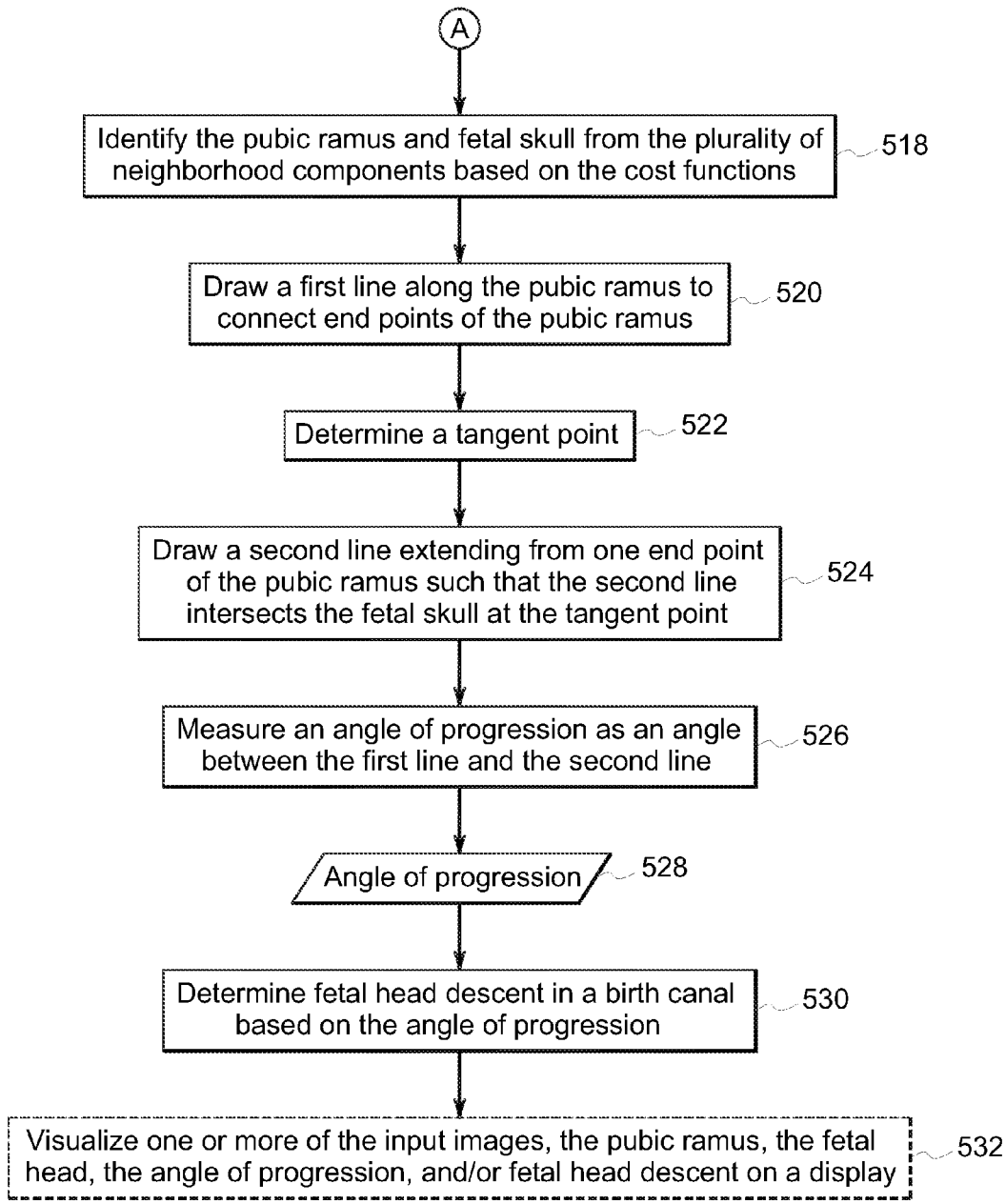
Figure 6C:
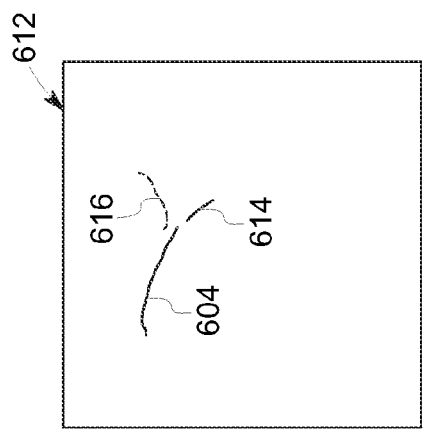
Figure 6F:
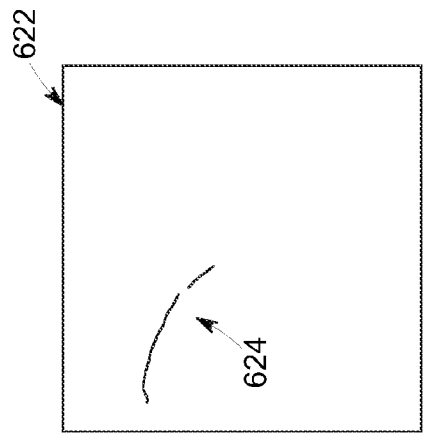
Figure 6B:
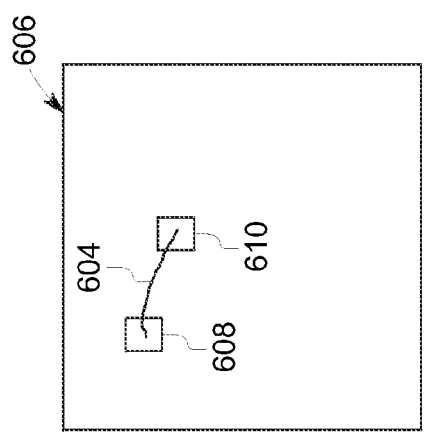
Figure 6E:
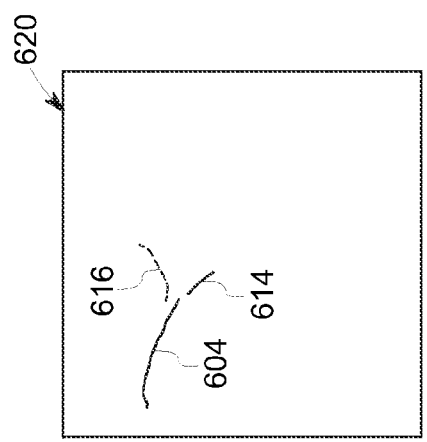
Figure 6A:
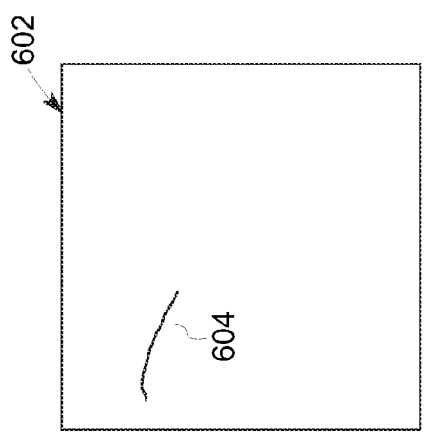
Figure 6D:
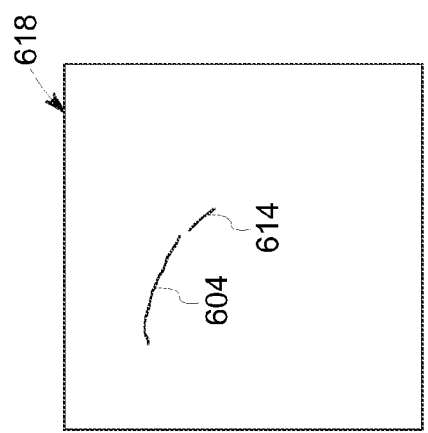

Turning now to FIG. 5, a flow chart of exemplary logic 500 for a method for monitoring fetal head descent in a birth canal of a patient during labor is illustrated. It may be noted that the method of FIG. 5 is described in terms of the various components of FIGS. 1-4. Moreover, the steps of the method of FIG. 5 may be performed by the FHDM platform 114 of FIG. 1.

The method 500 may be described in a general context of computer executable instructions. Generally, computer executable instructions may include routines, programs, objects, components, data structures, procedures, modules, functions, and the like that perform particular functions or implement particular abstract data types. In certain embodiments, the computer executable instructions may be located in computer storage media, such as a memory, local to an imaging system 108 (see FIG. 1) and in operative association with a processing subsystem. In certain other embodiments, the computer executable instructions may be located in computer storage media, such as memory storage devices, that are removed from the imaging system. Moreover, the method for automated monitoring of the fetal head descent in the birth canal of the patient during labor includes a sequence of operations that may be implemented in hardware, software, or combinations thereof.

As will be appreciated during a typical scan session, an object of interest such as a patient is positioned for imaging and the clinician attempts to image a desired anatomical region of interest in the patient. Accordingly, the method starts at step 502 where a patient, such as the patient in labor 102 is positioned for imaging. In the present example, the patient may be positioned in a supine position. The image acquisition device 106, such as an ultrasound probe may be placed transversely on the suprapubic region of the patient's abdominal region. A position of the fetal head may be visually identified. Furthermore, for determining progression of labor, the ultrasound probe 106 may be positioned on the perineum of the patient in labor in a mid-sagittal position between the labia and below the pubic symphysis. The position of the ultrasound probe 106 may be adjusted until an image is obtained that shows the sagittal view where the pubic ramus and the fetal skull are clearly visualized.

Once the patient in labor 102 is suitably positioned, one or more images 504 may be acquired, as indicated by step 502. In one embodiment, the acquired images include 2D transperineal ultrasound images 504. The acquired images 504 may be received by the acquisition subsystem 110, for example. It may be noted that the 2D images may include at least two bony landmarks such as the pubic ramus and the fetal head. It may be noted that in accordance with aspects of the present specification, fetal head descent in the birth canal during labor may be automatically monitored using a single acquired image. However, in certain other embodiments, more than one image may be employed to automatically monitor fetal head descent in the birth canal during labor.

Subsequent to the acquisition of the 2D transperineal ultrasound images 504, the images 504 may be processed by the processing subsystem 110 and by the FHDM platform 114 in particular to aid in determining/monitoring the progression of labor, as generally indicated by steps 506-532. The processing of steps 506-532 are described with described with reference to one image from the one or more images 504. The other images in the one or more images 504 may also be processed in a similar manner.

In accordance with aspects of the present specification, the input image 504 may be processed to automatically identify two anatomical structures of interest in the image 504. In one example, the two anatomical structures of interest may include two bony landmarks such as the pubic ramus and the fetal head/fetal head contour. In addition, the pubic ramus and the fetal head may be used to determine an angle of progression (AOP). The AOP may in turn be employed to determine a fetal head position in the birth canal of the patient in labor. It may be noted that the terms fetal head and fetal skull may be used interchangeably. Also, the terms fetal head contour and fetal skull contour may be used interchangeably.

Furthermore, as depicted by step 506, in order to facilitate the automated identification of the anatomical structures of interest such as the pubic ramus and the fetal head and the automated measurement of the AOP, the image 504 may be segmented into a plurality of neighborhood components. Segmenting the image 504 into a plurality of neighborhood components facilitates the identification of the pubic ramus and the fetal head. In one embodiment, a series of morphological operations may be used to segment the input image 504 into the plurality of neighborhood components. Some non-limiting examples of the morphological operations include processing the image 504 via a Frangi mask, a curvature mask, neighborhood component labeling, and the like.

It may be desirable to accurately locate the pubic ramus and the fetal head in the image 504. Typically, in an ideal ultrasound scan, the pubic ramus and the fetal head are characterized by uniform intensity, smooth curvature, and high amplitude. Additionally, the pubic ramus and the fetal head are also manifested as objects in the image 504 that are brighter than other components/objects in the vicinity. However, shadowing from the pubic symphysis affects the uniformity and brightness of the pubic ramus, thereby adversely impeding the delineation of the pubic ramus.

Furthermore, the tissue lining the pubic ramus and the fetal skull is typically continuous and coherent. However, in certain situations, the tissue may appear disjointed in the image 504 due to tissue occlusion, tissue alignment, and the like. It may therefore be desirable to smoothen across any spatial discontinuities in the tissue, while preserving the contrast between the tissue and the surrounding background to enhance the accuracy of identification of the pubic ramus and the fetal head in the image 504. It may also be desirable to remove any speckle in the image 504, while retaining the integrity of edges in the image 504.

Accordingly, the segmenting step 506 may further include enhancing contrast between the tissue and the surrounding background, as indicated by step 508. In addition, the segmenting step 506 may also include smoothening of the spatial discontinuities in the tissue, as depicted by step 510. In accordance with aspects of the present specification, a contrast enhancing and spatial smoothing filter may be employed to facilitate smoothening of the spatial discontinuities in the tissue, while preserving/enhancing the contrast between the tissue and the surrounding background.

In one example, tissue signatures corresponding to the pubic ramus and the fetal skull may be enhanced in the image 504. However, the contrast enhancement of step 508 may also result in other structures and/or noise in the image being highlighted, thereby impeding the selection of desired anatomical structures of interest, such as the pubic ramus and the fetal skull. It may therefore be desirable to enhance the accuracy of detection of the anatomical structures of interest in the image 504. Accordingly, the contrast enhanced image may be processed to transform the contrast enhanced image into a binary representation of image pixels that correspond to the pubic ramus and the fetal head, as indicated by step 512.

It may be noted that the pubic ramus and the fetal skull resemble ridge-like structures. Accordingly, at step 512, in one embodiment, the contrast enhanced image may be processed via use of a filter to enhance the contrast of thick tube-like or ridge-like structures in the image 504. By way of a non-limiting example, a Frangi vesselness filter/mask may be employed to enhance the contrast of the tube-like/ridge-like structures in the image 504. The filtered image may be referred to as a Frangi filtered image.

The contrast enhanced image may be convolved with a series of Gaussian second derivative filters. Furthermore, responses at each image pixel may be stacked in a [2×2] matrix to obtain the Hessian matrix D.

Furthermore, it may be noted that the ratio of eigenvalues of the matrix D (for example, $\lambda_1$ $\lambda_2$) is a measure of an isotropy of a corresponding structure of interest. The ratio of the eigenvalues having a small value is generally indicative of a ridge-like feature that has a determined orientation and therefore exhibits strong anisotropy. In one embodiment, the anisotropy may be emphasized by embedding the ratio of the eigenvalues into a functional form.

Furthermore, the Frangi filtered image $I_f$ may be binarized by selecting a threshold to generate a binary image $I_{fm}$. In one non-limiting example, a threshold value of about 0.5 may be employed to maximize the response of the Frangi mask/filter, while reducing the number of noisy components.

Consequent to the processing of the contrast enhanced image via the Frangi mask/filter, a binary image that includes one or more ridge-like structures is obtained. As previously noted, the pubic ramus and the fetal head resemble ridge-like structures. Consequently, the pubic ramus and the fetal head have a high curvature. Accordingly, it may be desirable to identify the desired anatomical structures of interest such as the pubic ramus and the fetal head from the one or more ridge-like structures in the binary image. In one embodiment, a pixel-wise curvature may be estimated from the contrast enhanced image based on equation (1).

$$I_c = div\left(\frac{\nabla I}{\|\nabla I\|}\right) \quad (1)$$

where I is the contrast enhanced image and $I_c$ is representative of an image obtained after processing the contrast enhanced image via use of a curvature transform.

As previously noted, the pubic ramus and the fetal skull have an intensity that is relatively brighter than the intensities of other structures of interest in the vicinity. Accordingly, a pixel that corresponds to a point on the pubic ramus or the fetal skull exhibits an intensity that is higher than the intensity of a neighboring pixel. In accordance with aspects of the present specification, a determined threshold value T may be employed to aid in selecting/identifying pixels that correspond to the pubic ramus. In one non-limiting example, a threshold value T having a value of about −0.3 may be used to delineate the anatomical structures of interest. Accordingly, the Frangi filtered image may be processed via use of a curvature mask represented by equation (2) to generate a curvature filtered image $I_{mc}$.

$$I_{mc} = \begin{cases} 1, & \text{if } I_c < T \\ 0, & \text{else} \end{cases} \quad (2)$$

In certain situations, the pubic ramus and fetal head/skull may not appear as distinct entities in the Frangi filtered image. However, the pubic ramus and the fetal skull may be connected to neighboring structures or noise. Moreover, in the curvature filtered image, the pubic ramus and the fetal head may have a distinct and a 'pruned' appearance and may be accompanied by many noise artifacts. In order to eliminate or minimize the pruned appearance and to remove the noise artifacts, the Frangi mask and the curvature mask may be combined to generate a combined mask. In one embodiment, the combined mask may be generated by a pixel-to-pixel AND operation of the Frangi filtered image and the curvature filtered image. A combined filtered image $I_{comb}$ may be generated via use of the combined mask.

Once the contrast enhanced image has been processed via one or more of the Frangi mask, the curvature mask, or the combined mask, an image having segmented neighborhood components may be obtained. Subsequently, at step 514, the neighborhood components in combined filtered image $I_{comb}$ may be annotated with labels. Each distinct neighborhood component in the combined filtered image $I_{comb}$ may be assigned a unique identifier or label, while the background is set to zero. An object or neighborhood component is usually defined as a set of connected, non-zero pixels, where two pixels being connected implies that it is possible to construct a path between the two pixels using only non-zero pixels between them. In one example, an 8-connected neighborhood function may be employed to construct the path between the two pixels. Furthermore, noise artifacts may be removed from the image. In one example, neighborhood components that have fewer than 50 pixels may be removed to eliminate the noise.

Following the processing of step 514, a neighborhood component labeled image is obtained. This image includes a plurality of labeled neighborhood components. It may be desirable to automatically select/identify the pubic ramus from the plurality of labeled neighborhood components.

Accordingly, at step 516, an objective cost function corresponding to each neighborhood component may be computed. In one embodiment, the objective function may be based on the pubic ramus anatomy, a size of the pubic ramus, a location of the pubic ramus, and the presentation of the pubic ramus in the image scanning plane. The pubic ramus is generally located in the top left half of the image. Accordingly, the location of the pubic ramus within the symphyseal capsule may be determined by a heuristic approach that is configured to identify objects in the top left half of the image. In addition, the pubic ramus appears as an object of high intensity and is typically brighter than other objects in the vicinity.

In accordance with further aspects of the present specification, a concavity of the component with respect to the lateral resolution may be used in the identification of the pubic ramus from the plurality of labeled neighborhood components. As previously noted, the pubic ramus and fetal skull are typically a continuous and coherent entity. However, in certain situations, the pubic ramus and the fetal head may appear discontinuous even in the contrast enhanced image. In accordance with aspects of the present specification, disjointed components in a local neighborhood may be "joined" with a candidate component based on similarity of curvature. In particular, disjointed components having similar curvature result in a lower value of fitting error. Hence, disjointed components in the neighborhood may be combined or joined with the candidate component based on a value of the fitting error.

Referring now to FIGS. 6(*a*)-6(*f*), diagrammatical representations of a method of joining or combining disjointed components with a candidate component for use in selection of a desired anatomical structure of interest, such as the pubic ramus are depicted. As depicted in an image 602 of FIG. 6(*a*), reference numeral 604 is generally representative of an initial candidate component. Furthermore, as depicted in an image 606 of FIG. 6(*b*), a neighborhood search may be performed to determine end points of the initial candidate component 604. Reference numerals 608 and 610 represent the two ends of the initial candidate labeled component 604.

Subsequently, a search may be carried out in the neighborhood of the two end points 608, 610 of the initial candidate component 604 to determine presence of any disjointed components, as depicted by an image 612 of FIG. 6(*c*). In the example of FIG. 6(*c*), the search may result in the determination of the presence of a first disjointed component 614 and a second disjointed component 616.

According to aspects of the present specification, the disjointed components may be combined or joined with the initial candidate component 604 based on a similarity of curvature of the components, as depicted by an image 618 of FIG. 6(*d*) and an image 620 of FIG. 6(*e*). Accordingly, normalized fitting errors corresponding to the disjointed components may be determined. In particular, as depicted in FIG. 6(*d*), a normalized fitting error corresponding to combining the initial candidate component 604 and the first disjointed component 612 may be determined. Similarly, a normalized fitting error corresponding to combining the initial candidate component 604 and the second disjointed component 614 may be determined, as indicated by FIG. 6(*e*).

Subsequently, the determined fitting errors may be compared with a determined threshold value to identify a 'best fit' of the disjointed components with the initial candidate component 604 based on the similarity of curvature of the components to be joined or combined. In the present example, the first component 614 that has a normalized fitting error within the threshold value may be combined with the initial candidate component 604, as depicted in FIG. 6(*d*). Also, as indicated in FIG. 6(*e*), the second component 616 that has a normalized fitting error outside the threshold value may be discarded.

Consequently, the first disjointed component 612 may be combined or joined with the initial candidate component 604 to obtain a combined component 624 as depicted in an image 622 of FIG. 6(*f*). The combined component 624 may then be used in the selection of the pubic ramus from the plurality of labeled neighborhood components.

Referring again to FIG. 5, at step 518, a component representative of the pubic ramus may be selected from the plurality of labeled neighborhood components. In one embodiment, the selection of the desired component such as the pubic ramus may be based on the cost function, as depicted by step 516. In one embodiment, the cost function may be based on a length of the component, an intensity of the component, vesselness, and the concavity of the component. The process of selecting a component as the pubic ramus may be represented as:

$$R_c = \underset{i \in 1,2,\ldots,N_r}{\arg\max}(C_i + mV_i + mI_i + l_i) \qquad (3)$$

where, $C_i$, $mV_i$, $mI_i$, $l_i$ are measures of concavity, mean vesselness, mean intensity, and length of the $i^{th}$ component, respectively, $N_r$ is the total number of components after combining disjointed components located in the top left half of the imaging scan plane, and $R_c$ is representative of a component that is selected as the pubic ramus.

Additionally, at step 518, once the pubic ramus is identified, it is desirable to select the fetal head/skull from the plurality of labeled neighborhood components. A component from the plurality of labeled neighborhood components that represents a leading edge of the fetal skull may be selected based on a cost function. In one example, the cost function may be computed based on the fetal skull anatomy, a location of the fetal skull anatomy, and a presentation of the fetal skull anatomy in an imaging scan plane. Furthermore, the fetal skull may be assumed to be located below the pubic ramus in the image. Moreover, the fetal skull appears as an object of high intensity in the image and is typically brighter than other objects in the vicinity.

As previously noted with reference to the selection of the pubic ramus, the concavity of the component with respect to the lateral direction may be used to aid in the selection of the fetal skull from the plurality of labeled neighborhood components. Accordingly, disjointed components may be combined to obtain a combined component. Furthermore, a component representative of the fetal skull may be selected from the plurality of labeled neighborhood components based on the cost function. One example of the cost function is provided in equation (4).

$$H_c = \underset{\substack{i \in 1,2,\ldots,N_h,\\ i \text{ liesbelow} R_c}}{\arg\max} (C_i + mV_i + mI_i + l_i) \quad (4)$$

where $N_h$ is the total number of components that lie within the search constraint and $H_c$ is representative of a component selected as the fetal skull.

Consequent to the processing of steps 506-518, the pubic ramus and the fetal skull are identified in the image 504. Subsequently, it is desirable to measure the AOP. In accordance with exemplary aspects of the present specification, the AOP is representative of an angle between the two bony landmarks such as the fetal skull and the maternal pubic ramus that are identified using the 2D transperineal ultrasound images 504. In particular, the angle of progression is defined as the angle between the ramus line and the tangent line.

As previously noted, the ramus line is defined as a line that passes through the two end points of the pubic ramus. Accordingly, at step 520, the ramus line may be determined. To that end, a first end point and a second point of the pubic ramus may be identified. Subsequently, a first line representative of the ramus line may be drawn such that the first line passes through the two end points of the pubic ramus.

Furthermore, the tangent line is defined as a line that starts from the inferior apex of the pubic ramus (for example, the right end point) and intersects the fetal skull contour tangentially. In one embodiment, a second line that is representative of the tangent line may be drawn from the inferior apex, for example, the second end point of the pubic ramus such that the second line intersects the fetal skull contour tangentially. It is therefore desirable to determine a point where the second line intersects the fetal skull tangentially, as depicted by step 522. This point may be referred to as a tangent point.

Turning now to FIG. 7, a diagrammatical representation 700 of a method of determining a tangent point of step 522 of FIG. 5 is depicted. Reference numeral 702 is representative of an image that includes the pubic ramus 704 and the fetal head or fetal skull contour 706. As noted hereinabove, the tangent point is a point where the second line extending from the inferior apex of pubic ramus 704 intersects the fetal skull contour 706 tangentially.

In on example, the fetal skull contour may be modeled by a polynomial regression equation represented by:

$$P = p_n x^n + p_{n-1} x^{n-1} + \ldots + p_1 x + p_0 x \quad (5)$$

where, n=2, 3, represent quadratic and cubic regression models, respectively.

As depicted in FIG. 7, the pubic ramus has a first end point 708 $(x_1, y_1)$ and a second end point 710 $(x_2, y_2)$. Reference numeral 712 may be representative of a plurality of points on the fetal skull contour 706. In accordance with aspects of the present specification, for a given candidate point 712 located on the fetal skull contour 706, two slopes $s_1$ and $s_2$ may be computed. A first slope $s_1$ is representative of a slope of a tangent line 714 to the curve P that is representative of the fetal skull contour 706 at a candidate point 712 on the fetal skull contour 706. Moreover, a second slope $s_2$ is representative of the slope of a line 716 extending from the inferior apex 710 of the pubic ramus 704 to the candidate point 712. Subsequently, the two slopes $s_1$ and $s_2$ may be computed for each point 712 on the fetal skull contour 706. The tangent point may be selected by comparing the two slopes $s_1$ and $s_2$ for each point 712 on the fetal skull contour 706. In particular, a candidate point 712 where the two corresponding slopes $s_1$ and $s_2$ have a minimum absolute difference may be identified as the tangent point $(x_t, y_t)$. In the example of FIG. 6, a tangent point 718 may be identified subsequent to the determination of the slopes corresponding to the candidate points 712. The tangent point $(x_t, y_t)$ may be computed as depicted in equation (6).

$$(x_t, y_t) = \underset{(x_i, y_i) \in H_c, n \in \{2,3\}}{\arg\max} \left\| (np_n x_i^{n-1} + (n-1)p_{n-1} x_i^{n-2} \ldots + p_1) - \left(\frac{(y_i - y_2)}{(x_i - x_2)}\right) \right\|_1 \quad (6)$$

where $H_c$ is the fetal skull contour, $(x_2, y_2)$.) is the right end point 710 of the pubic ramus 704, and $(x_t, y_t)$ is the computed tangent point.

With returning reference to FIG. 5, subsequent to the determination of the tangent point, the second line representative of the tangent line may be drawn from the right end point 710 of the pubic ramus 704 such that the second line intersects the fetal skull contour 706 tangentially at the tangent point, as depicted by step 524.

Once the ramus line and the tangent line have been drawn/determined, an AOP may be measured, as indicated by step 526. As previously noted, in accordance with exemplary aspects of the present specification, the AOP is measured as the angle between the ramus line and the tangent line. Reference numeral 528 may be representative of the angle of progression.

FIG. 8 is a diagrammatical representation 800 of a method of measuring an angle of progression (AOP) of step 528 of FIG. 5. The measurement of the AOP 802 may be described with reference to the elements of FIG. 7. In accordance with aspects of the present specification, the AOP 802 may be measured as the angle between a ramus line 804 that joins the two end points 708 and 710 of the pubic ramus 704 and a tangent line 806 that extends from the end point 710 and intersects the fetal skull contour 706 at the tangent point 718 on the fetal skull contour 704.

Referring again to FIG. 5, the AOP 528 so determined may be used to evaluate the position of the fetal head in the birth canal of the patient in labor, as indicated by step 530. In one embodiment, a look-up table may be used to determine a fetal head station based on the value of the AOP 528.

Furthermore, one or more of the input images, the pubic ramus, the fetal skull contour, the tangent point, the tangent line, the ramus line, the AOP, and the fetal head descent may be visualized on a display, such as the display 118 of FIG. 1. The visual display provides the clinician or staff in the labor room a visual representation of the various parameters and the current position of the fetus in the birth canal, thereby enhancing clinical workflow.

Turning now to FIGS. 9(a)-9(i), diagrammatical representations of the automated method of measuring the angle of progression of FIG. 5 are illustrated. FIG. 9(a) is representative of an input labor and delivery image 902, such as a 2D transperineal ultrasound image. Furthermore, FIG. 9(b) is representative of a contrast enhanced image 904. Moreover, a Frangi filtered image 906 is depicted in FIG. 9(c), while FIG. 9(d) illustrates a binary image 908 generated by thresholding the Frangi filtered image with a threshold of 0.5. Also, a curvature filtered image 910 is depicted in FIG. 9(e). Also, FIG. 9(f) depicts a Frangi filtered image 912 showing the pubic ramus and the fetal skull contour, while a curvature image 914 with the pubic ramus and the fetal skull contour is illustrated in FIG. 9(g).

In addition, in FIG. 9(h), a combined mask 916 generated by combining the Frangi filter mask and the curvature mask is depicted. FIG. 9(i) illustrates an image 918 showing the neighborhood components with an 8-neighborhood connectivity in the combined image.

FIG. 10 depicts a comparison 1000 of a traditional manual measurement of the angle of progression with the fully automated measurement of the AOP afforded by the systems and methods of the present specification. It may be noted that based on a logistic regression analysis, a strong agreement between the two AOP measurements with $R^2$ measure of fit as high as 97.8% for good quality images may be obtained. In addition, an overall $R^2$ measure of fit of about 84.0% may be obtained. It may be noted that the automated AOP measurement lies with +/−5° bounds of the manual measurements for a majority of images.

As previously noted with reference to FIG. 1, the medical imaging system 106 may include an ultrasound imaging system. FIG. 10 is a block diagram of an embodiment of an ultrasound imaging system 1100 depicted in FIG. 1. The ultrasound system 1100 includes an acquisition subsystem, such as the acquisition subsystem 110 of FIG. 1 and a processing subsystem, such as the processing subsystem 112 of FIG. 1. The acquisition subsystem 110 may include a transducer assembly 1106. In addition, the acquisition subsystem 110 includes transmit/receive switching circuitry 1108, a transmitter 1110, a receiver 1112, and a beamformer 1114. It may be noted that in certain embodiments, the transducer assembly 1106 is disposed in the probe 104 (see FIG. 1). Also, in certain embodiments, the transducer assembly 1106 may include a plurality of transducer elements (not shown) arranged in a spaced relationship to form a transducer array, such as a one-dimensional or two-dimensional transducer array, for example. Additionally, the transducer assembly 1106 may include an interconnect structure (not shown) configured to facilitate operatively coupling the transducer array to an external device (not shown), such as, but not limited to, a cable assembly or associated electronics. In the illustrated embodiment, the interconnect structure may be configured to couple the transducer array to the T/R switching circuitry 1108.

The processing subsystem 112 includes a control processor 1116, a demodulator 1118, an imaging mode processor 1120, a scan converter 1122 and a display processor 1124. The display processor 1124 is further coupled to a display monitor 1136, such as the display 116 (see FIG. 1), for displaying images. User interface 1138, such as the user interface area 118 (see FIG. 1), interacts with the control processor 1116 and the display monitor 1136. The control processor 1116 may also be coupled to a remote connectivity subsystem 1126 including a remote connectivity interface 1128 and a web server 1130. The processing subsystem 112 may be further coupled to a data repository 1132, such as the data repository 114 of FIG. 1, configured to receive and/or store ultrasound image data. The data repository 1132 interacts with an imaging workstation 1134.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the invention. Thus, those skilled in the art will appreciate that the present ultrasound imaging system 1100 is provided by way of example, and the present specifications are in no way limited by the specific system configuration.

In the acquisition subsystem 110, the transducer assembly 1106 is in contact with the patient 102. The transducer assembly 1106 is coupled to the transmit/receive (T/R) switching circuitry 1108. Also, the T/R switching circuitry 1108 is in operative association with an output of transmitter 1110 and an input of the receiver 1112. The output of the receiver 1112 is an input to the beamformer 1114. In addition, the beamformer 1114 is further coupled to the input of the transmitter 1110 and to the input of the demodulator 1118. The beamformer 1114 is also operatively coupled to the control processor 1116 as shown in FIG. 13.

In the processing subsystem 112, the output of demodulator 1118 is in operative association with an input of the imaging mode processor 1120. Additionally, the control processor 1116 interfaces with the imaging mode processor 1120, the scan converter 1122 and the display processor 1124. An output of imaging mode processor 1120 is coupled to an input of scan converter 1122. Also, an output of the scan converter 1122 is operatively coupled to an input of the display processor 1124. The output of display processor 1124 is coupled to the monitor 1136.

Furthermore, the foregoing examples, demonstrations, and process steps such as those that may be performed by the system may be implemented by suitable code on a processor-based system, such as a general-purpose or special-purpose computer. It should also be noted that different implementations of the present specification may perform some or all of the steps described herein in different orders or substantially concurrently, that is, in parallel. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may include paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

The various systems and methods for automated monitoring of the fetal head descent in the birth canal of the patient during labor described hereinabove provide a framework for robust automated measurement of the angle of progression, thereby simplifying workflow in the labor room especially for less experienced users. Moreover, the systems and method presented herein may also be extended to measure alternate markers for fetal head descent such as the head-perineum distance. The systems and method also allow an independent and objective assessment of image quality in terms of the visualization and presentation of the fetal skull and the pubic ramus.

Additionally, the various systems and methods are automated, thereby circumventing the need for manual intervention. Consequently, dependency on highly trained professionals is reduced. In addition, the scan time may be dramatically minimized when compared to manual image acquisition and measurement, thereby increasing the throughput. By way of example, for rural setups with high volumes of fetal scanning, these systems and methods aid in decreasing the net scan time, thereby enhancing handling of higher volumes.

Furthermore, the systems and methods that are capable of automatically measuring the angle of progression by ultrasound aid in enhancing the accuracy of monitoring of the fetal head descent by reducing the variability in assisting patients during labor. Moreover, the productivity may be increased by avoiding multiple examinations and/or minimizing the need for support of expert clinicians to assess the head station. Also, the systems and method provide an objective and reproducible documentation that is independent of the experience levels of midwives or clinicians assisting in the labor room. The easy and fast workflow derived provided by the methods and systems for the angle of progression measurement may aid in enhancing the skill and utilization of midwives or paramedics across the world and also encourage adoption of ultrasound to assist labor in geographies with fewer experienced sonographers.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A method for automatically monitoring fetal head descent in a birth canal, comprising:
   acquiring, via at least one processor, one or more transperineal ultrasound images corresponding to a birth canal of a patient in labor such that the one or more transperineal ultrasound images comprise at least two structures of interest;
   segmenting, via the at least one processor, each of the one or more transperineal ultrasound images into a plurality of neighborhood components;
   determining, via the at least one processor, a cost function corresponding to each neighborhood component in the plurality of neighborhood components in each of the one or more transperineal ultrasound images;
   identifying, via the at least one processor, the at least two structures of interest in each of the one or more transperineal ultrasound images based on the cost function, wherein the at least two structures of interest comprise a pubic ramus and a fetal head;
   measuring, via the at least one processor, an angle of progression between a first line passing through the pubic ramus and a second line extending from an inferior apex of the pubic ramus and tangentially intersecting a contour of the fetal skull;
   determining, via the at least one processor, the fetal head descent in the birth canal based on the angle of progression to automatically monitor progression of the fetal head in the birth canal of the patient during labor; and
   visualizing the one or more transperineal ultrasound images, the pubic ramus, the fetal head, a tangent point on the fetal head, the angle of progression, the fetal head descent, or combinations thereof on a display, wherein at least the angle of progression is overlaid on the one or more transperineal ultrasound images,
   wherein the steps of acquiring the one or more transperineal ultrasound images, segmenting each of the one or more transperineal ultrasound images, determining the cost function, identifying the at least two structures of interest, measuring the angle of progression, determining the fetal head descent, and visualizing are automated steps.

2. The method of claim 1, wherein the one or more transperineal ultrasound images comprise two-dimensional transperineal ultrasound images.

3. The method of claim 1, wherein segmenting each of the one or more transperineal ultrasound images further comprises enhancing a contrast of each of the one or more transperineal ultrasound images to generate a corresponding contrast enhanced image.

4. The method of claim 3, wherein segmenting each of the one or more transperineal ultrasound images further comprises smoothening spatial discontinuities in tissues in each of the one or more transperineal ultrasound images.

5. The method of claim 4, wherein smoothening spatial discontinuities in the tissues in each of the one or more transperineal ultrasound images comprises processing the corresponding contrast enhanced image via use of a filter to generate a corresponding contrast enhanced smoothened image.

6. The method of claim 5, wherein segmenting each of the one or more transperineal ultrasound images further comprises processing the corresponding contrast enhanced smoothened image via a Frangi mask, a curvature mask, or a combined mask to generate a corresponding filtered image.

7. The method of claim 6, further comprising labeling the plurality of neighborhood components in each of the one or more transperineal ultrasound images.

8. The method of claim 1, wherein determining the cost function comprises computing the cost function corresponding to each neighborhood component in each of the one or more transperineal ultrasound images based on a location of the neighborhood component, a size of the neighborhood component, an anatomical presentation of the neighborhood component, or combinations thereof.

9. The method of claim 1, wherein measuring the angle of progression comprises:
   identifying end points of the pubic ramus; and
   drawing the first line to connect the end points of the pubic ramus.

10. The method of claim 9, further comprising determining a tangent point on the fetal head.

11. The method of claim 10, further comprising drawing the second line from one end point of the pubic ramus such that the second line intersects the fetal head tangentially at the tangent point on the fetal head.

12. The method of claim 11, wherein measuring the angle of progression comprises measuring an angle subtended between the first line and the second line.

13. The method of claim 12, wherein determining the fetal head descent in the birth canal based on the angle of progression comprises identifying a fetal station based on a look-up table, and wherein the look-up table provides a correspondence between the angle of progression and the fetal station.

14. A system, comprising:
   at least one processor configured to automatically:
      obtain one or more transperineal ultrasound images corresponding to a birth canal of a patient in labor such that the one or more transperineal ultrasound images comprise at least two structures of interest;

segment each of the one or more transperineal ultrasound images into a plurality of neighborhood components;

determine a cost function corresponding to each neighborhood component in the plurality of neighborhood components in each of the one or more transperineal ultrasound images;

identify the least two structures of interest in each of the one or more transperineal ultrasound images based on the cost function, wherein the at least two structures of interest comprise a pubic ramus and a fetal head;

measure an angle of progression between a first line passing through the pubic ramus and a second line extending from an inferior apex of the pubic ramus and tangentially intersecting a contour of the fetal skull;

determine fetal head descent in the region of interest in the object of interest based on the angle of progression; and visualize the one or more transperineal ultrasound images, the pubic ramus, the fetal head, a tangent point on the fetal head, the angle of progression, the fetal head descent, or combinations thereof on a display, wherein at least the angle of progression is overlaid on the one or more transperineal ultrasound images.

15. A computer-readable non-transitory media storing computer executable code to perform the method of:

acquiring one or more transperineal ultrasound images corresponding to a birth canal of a patient in labor such that the one or more transperineal ultrasound images comprise at least two structures of interest;

segment each of the one or more transperineal ultrasound images into a plurality of neighborhood components;

determine a cost function corresponding to each neighborhood component in the plurality of neighborhood components in each of the one or more transperineal ultrasound images;

identify the at least two structures of interest in each of the one or more transperineal ultrasound images based on the cost function, wherein the at least two structures of interest comprise a pubic ramus and a fetal head;

measure an angle of progression between a first line passing through the pubic ramus and a second line extending from an inferior apex of the pubic ramus and tangentially intersecting a contour of the fetal skull;

determine fetal head descent in the birth canal based on the angle of progression; and visualize the one or more transperineal ultrasound images, the pubic ramus, the fetal head, a tangent point on the fetal head, the angle of progression, the fetal head descent, or combinations thereof on a display, wherein at least the angle of progression is overlaid on the one or more transperineal ultrasound images, wherein the steps of acquiring the one or more transperineal ultrasound images, segmenting each of the one or more transperineal ultrasound images, determining the cost function, identifying the at least two structures of interest, measuring the angle of progression, determining the fetal head descent, and visualizing are automated steps.

16. An imaging system, the system comprising:

an ultrasound imaging system configured to obtain one or more transperineal ultrasound images corresponding to a birth canal of a patient in labor such that the one or more transperineal ultrasound images comprise at least two structures of interest;

at least one processor in operative association with the ultrasound imaging system, wherein the at least one processor is configured to automatically:

segment each of the one or more transperineal ultrasound images into a plurality of neighborhood components;

determine a cost function corresponding to each neighborhood component in the plurality of neighborhood components in each of the one or more transperineal ultrasound images;

identify the at least two structures of interest in each of the one or more transperineal ultrasound images based on the cost function, wherein the at least two structures of interest comprise a pubic ramus and a fetal head;

measure an angle of progression between a first line passing through the pubic ramus and a second line extending from an inferior apex of the pubic ramus and tangentially intersecting a contour of the fetal skull;

determine fetal head descent in the birth canal based on the angle of progression; and visualize the one or more transperineal ultrasound images, the pubic ramus, the fetal head, a tangent point on the fetal head, the angle of progression, the fetal head descent, or combinations thereof on a display, wherein at least the angle of progression is overlaid on the one or more transperineal ultrasound images.

17. The imaging system of claim 16, further comprising the display configured to visualize the one or more transperineal ultrasound images, the pubic ramus, the fetal head, the tangent point on the fetal head, the angle of progression, the fetal head descent, or combinations thereof thereon.

* * * * *